(12) United States Patent
Taniguchi et al.

(10) Patent No.: US 11,122,988 B2
(45) Date of Patent: Sep. 21, 2021

(54) MAGNETIC RESONANCE IMAGING APPARATUS

(71) Applicant: HITACHI, LTD., Tokyo (JP)

(72) Inventors: Yo Taniguchi, Tokyo (JP); Suguru Yokosawa, Tokyo (JP); Hisaaki Ochi, Tokyo (JP); Toru Shirai, Tokyo (JP); Shinji Kurokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1300 days.

(21) Appl. No.: 15/107,540

(22) PCT Filed: Aug. 6, 2015

(86) PCT No.: PCT/JP2015/072424
§ 371 (c)(1),
(2) Date: Jun. 23, 2016

(87) PCT Pub. No.: WO2017/022136
PCT Pub. Date: Feb. 9, 2017

(65) Prior Publication Data
US 2017/0209067 A1 Jul. 27, 2017

(51) Int. Cl.
A61B 5/055 (2006.01)
G01R 33/56 (2006.01)
(Continued)

(52) U.S. Cl.
CPC ............ *A61B 5/055* (2013.01); *G01R 33/387* (2013.01); *G01R 33/5608* (2013.01);
(Continued)

(58) Field of Classification Search
None
See application file for complete search history.

(56) References Cited

U.S. PATENT DOCUMENTS

2008/0129298 A1* 6/2008 Vaughan ............ G01R 33/5659
324/322

FOREIGN PATENT DOCUMENTS

JP 2007-020859 A 2/2007
JP 2011-024926 A 2/2011

OTHER PUBLICATIONS

Funai, A. K. (2011) "Regularized Estimation of Main and RF Field Inhomogeneity and Longitudinal Relaxation Rate in Magnetic Resonance Imaging." [Doctoral dissertation, University of Michigan], Dissertations and Theses (Ph.D. and Master's). http://hdl.handle.net/2027.42/86473 (Year: 2011).*

(Continued)

*Primary Examiner* — Luther Behringer
(74) *Attorney, Agent, or Firm* — Mattingly & Malur, PC

(57) ABSTRACT

A technology of improving image quality of a calculation image or parameter estimation accuracy even in a case where a method of simultaneously generating calculation images of a plurality of parameters is used is provided. Thus, by utilization of a reconstructed image in an optimal resolution of each parameter to be estimated, a value of the parameter is estimated and a calculation image that is a distribution of the value of the parameter is acquired. A reconstructed image in an optimal resolution is acquired by adjustment of a resolution of a reconstructed image acquired in an optimal resolution of an estimation parameter with the highest optimal resolution among parameters to be estimated in scanning. Alternatively, in scanning, only a reconstructed image used for calculation of a predetermined parameter to be estimated is acquired in an optimal resolution of the parameter to be estimated.

7 Claims, 13 Drawing Sheets

(51) Int. Cl.
  *G01R 33/387*  (2006.01)
  *G01R 33/565*  (2006.01)
  G01R 33/24  (2006.01)
  G01R 33/483  (2006.01)
  G01R 33/561  (2006.01)
  G01R 33/50  (2006.01)
(52) U.S. Cl.
  CPC ...... *G01R 33/56536* (2013.01); *G01R 33/246* (2013.01); *G01R 33/4835* (2013.01); *G01R 33/50* (2013.01); *G01R 33/5602* (2013.01); *G01R 33/5616* (2013.01)

(56) References Cited

OTHER PUBLICATIONS

International Search Report of PCT/JP2015/072424 dated Nov. 2, 2015.
International Preliminary Report on Patentability received in corresponding International Application No. PCT/JP2015/072424 dated Feb. 15, 2018.

\* cited by examiner

FIG. 4
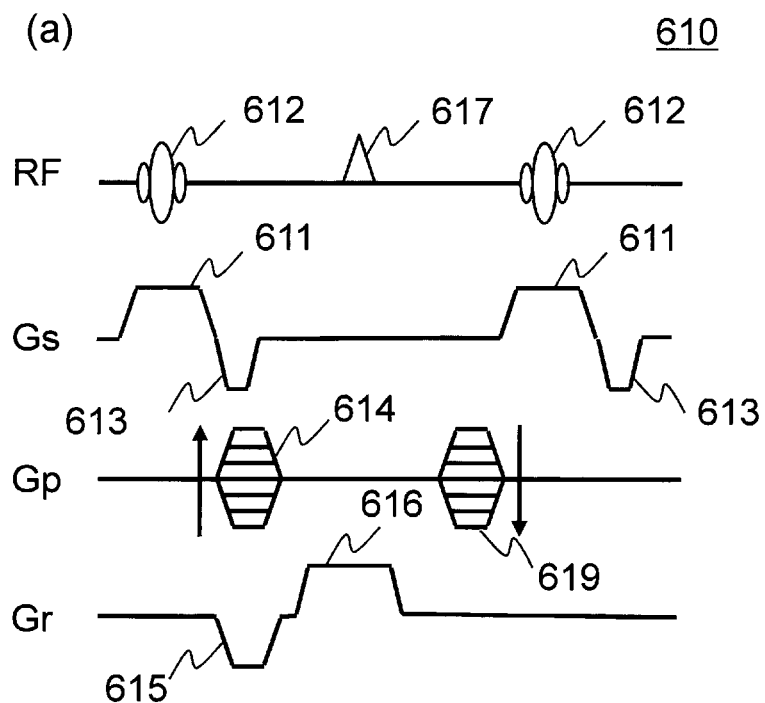
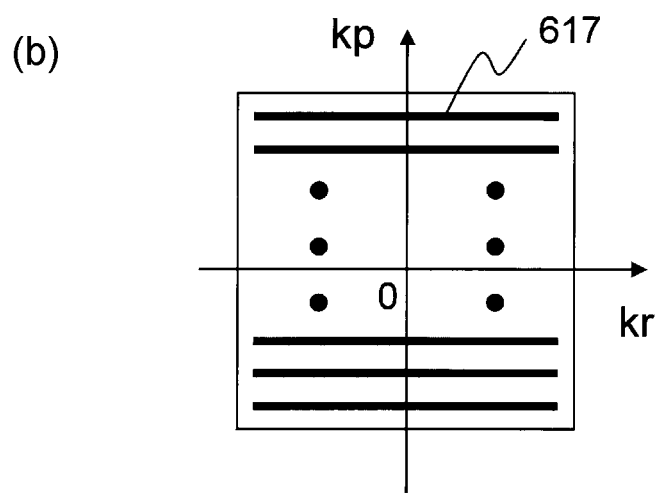

FIG. 10
(a) 513
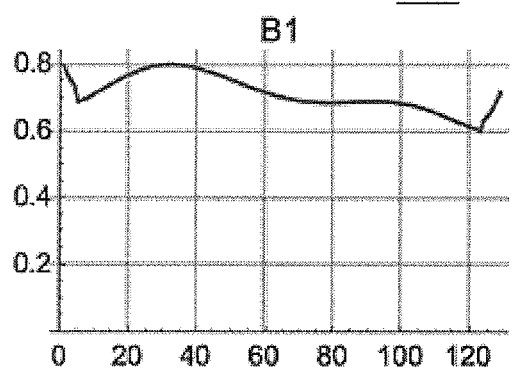
(b) 523
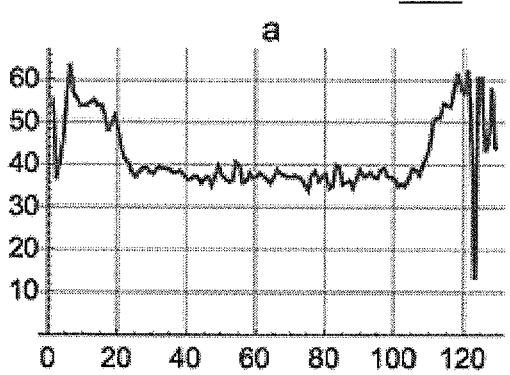
(c) 514
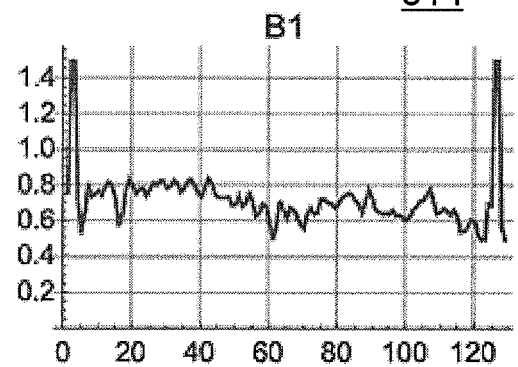
(d) 524
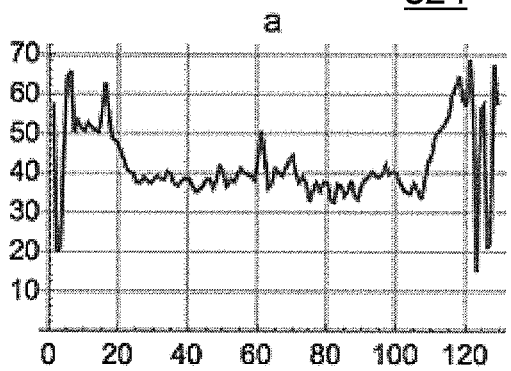

FIG. 11
(a)
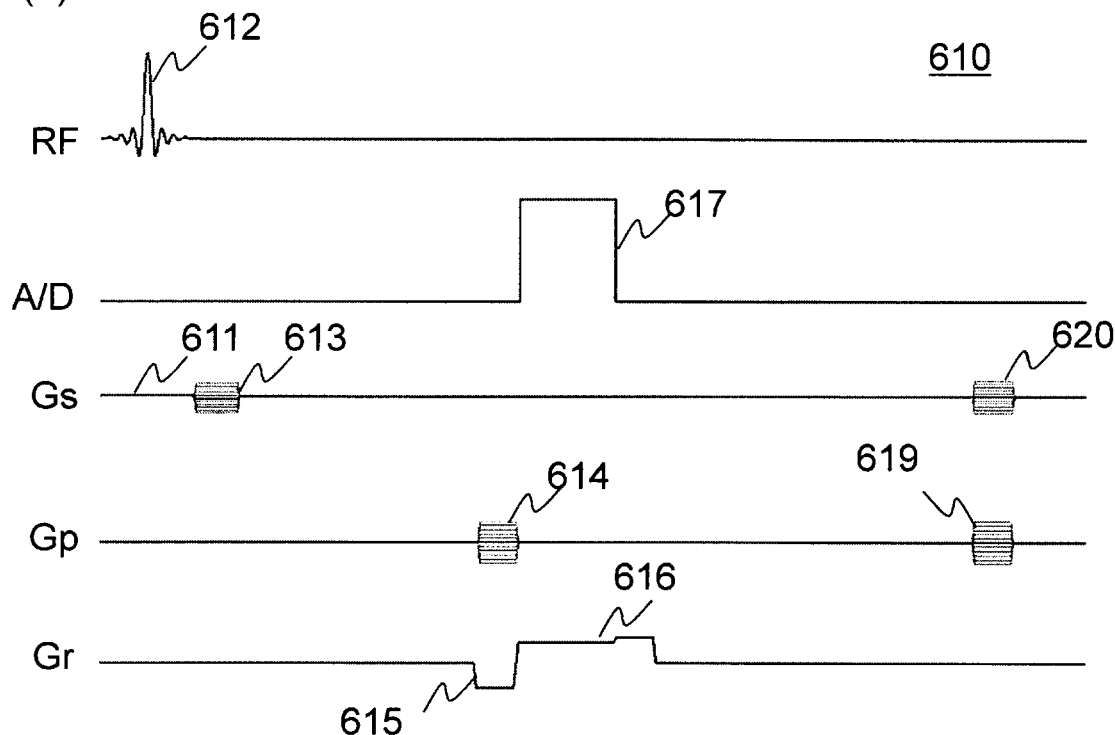
(b)
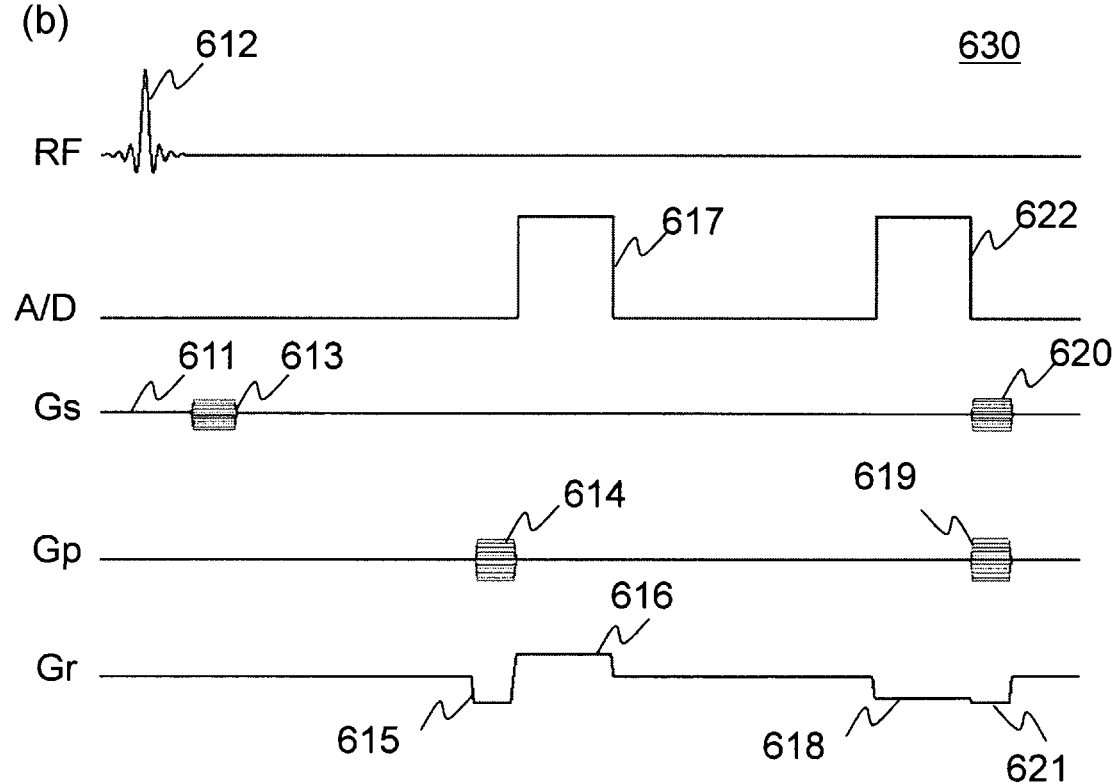

FIG. 14
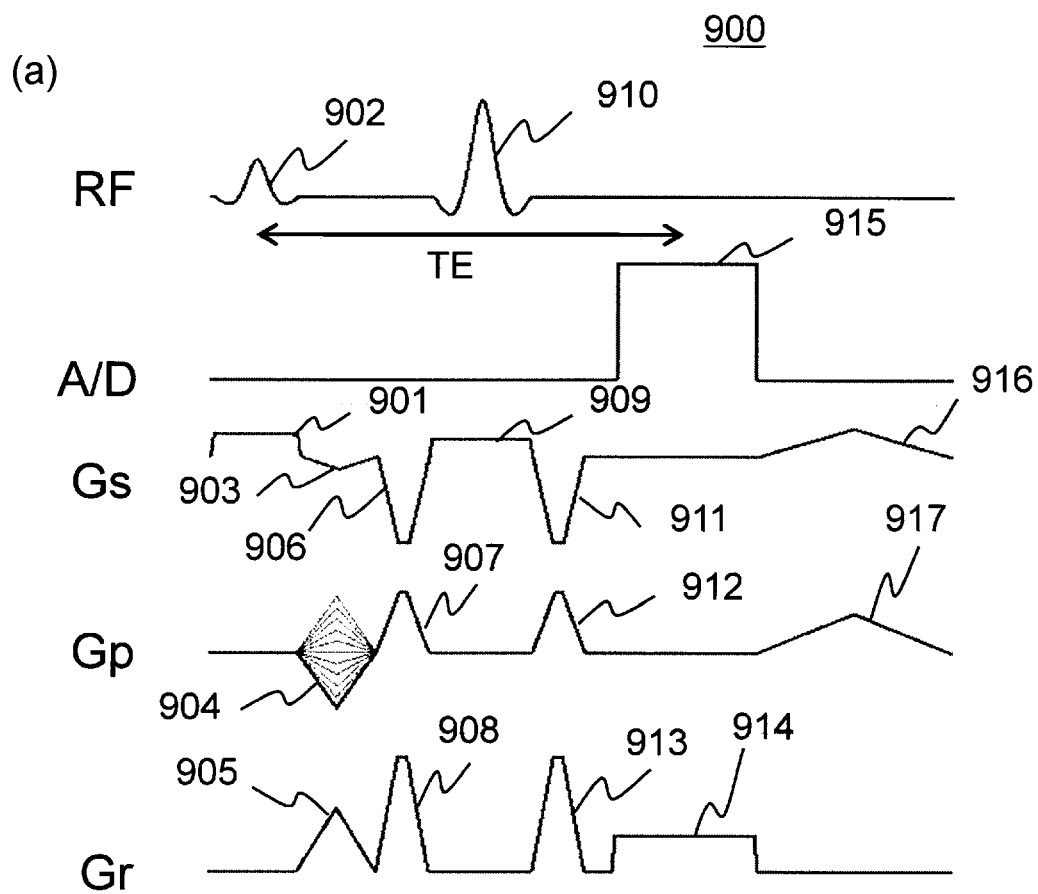
(a)
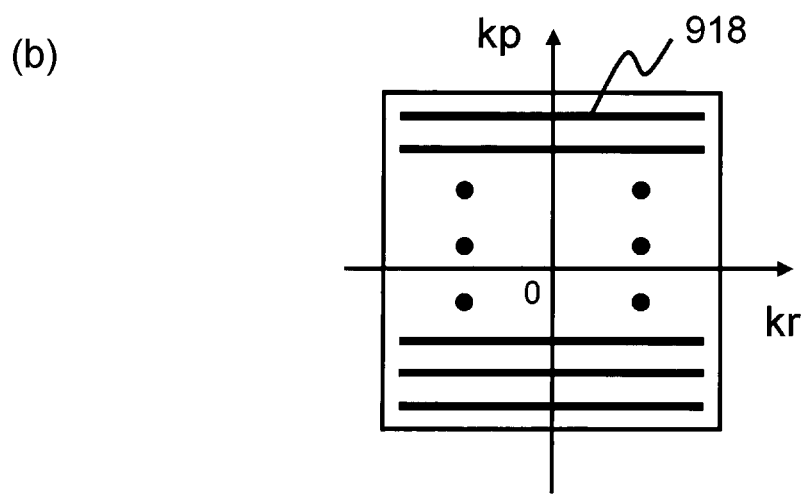
(b)

MAGNETIC RESONANCE IMAGING APPARATUS

TECHNICAL FIELD

The present invention relates to a magnetic resonance imaging (MRI) technology. Specifically, the present invention relates to a technology of estimating a subject parameter by calculation.

BACKGROUND ART

An MRI apparatus is a medical image diagnosis apparatus that causes a hydrogen nucleus in an arbitrary plane crossing a subject to generate nuclear magnetic resonance and that scans a tomographic image in the plane based on a generated nuclear magnetic resonance signal (NMR signal; echo signal). Generally, a slice magnetic field gradient to specify a scanning surface is applied and an excitation pulse to excite a magnetization in the surface is simultaneously given, whereby an echo signal generated in a stage in which a magnetization excited thereby converges is acquired. Here, in order to give positional information to the magnetization, a phase encoding magnetic field gradient and a readout magnetic field gradient in directions orthogonal to each other in a tomographic surface are applied in a period from the excitation to acquisition of the echo signal.

An excitation pulse for generation of the echo signal and each magnetic field gradient to give positional information are applied based on a previously-set pulse sequence. Various kinds of pulse sequences are known according to purposes. For example, in a gradient echo (GE) type high-speed scanning method, the pulse sequence is repeatedly operated and a phase encoding magnetic field gradient is serially changed in each time of the repetition, whereby echoes the number of which is necessary for acquiring one tomographic image are serially measured.

In MRI, an image is generally acquired by reconstruction of an acquired echo signal. In addition, there is a quantitative value image (calculation image, parameter distribution, and parameter map) acquired by calculation of an intended quantitative value of each pixel from a plurality of images acquired by execution of a pulse sequence with different scan parameters. The calculated quantitative value includes a subject parameter, an apparatus parameter, and the like.

The scan parameter is a parameter that is set in scanning and is, for example, repetition time, set strength of a radio frequency magnetic field, or a phase of a radio frequency magnetic field. The subject parameter is a physical property of a subject or a value depending on that which parameter is, for example, longitudinal relaxation time T1, transverse relaxation time T2, spin density $\rho$, a resonance frequency f0, a diffusion coefficient D, or an irradiation strength distribution of a radio frequency magnetic field ($B_1$ distribution). The apparatus parameter is a parameter that depends on an MRI apparatus, which is used in scanning, such as magnetic field strength $B_0$, or a sensitivity distribution of a receiver coil $S_c$.

Generally, a relationship between a scan parameter, a subject parameter, or an apparatus parameter and a pixel value is analytically calculated as a signal function and the above-described quantitative value is acquired by utilization of this signal function. However, a signal function is not analytically calculated depending on a pulse sequence. In a case of such a pulse sequence, there is a method of generating a calculation image by creating a signal function by numerical simulation (see, for example, PTL 1).

CITATION LIST

Patent Literature

PTL 1: Japanese Patent Application Laid-Open No. 2011-024926

SUMMARY OF INVENTION

Technical Problem

An optimal resolution of a calculation image varies depending on a parameter to be estimated. For example, since a $B_1$ distribution that is a subject parameter changes smoothly in a space, a high resolution is not necessary compared to T1 and T2 distributions. In a case of a conventional method of measuring and calculating parameters separately, a calculation image can be calculated in a resolution that is optimal to each parameter.

However, in the method disclosed in PTL 1, calculation images of a plurality of subject parameters and apparatus parameters are generated simultaneously. Thus, all calculation images are calculated with a resolution being fixed to that of a parameter having the highest optimal resolution. For example, in simultaneous calculation of distributions of $B_1$, T1, T2, and $\rho$, a resolution of the $B_1$ distribution is calculated in a high resolution similarly to the other distributions. However, when a calculation image of a parameter that does not need a high resolution (such as $B_1$ distribution) is calculated in a high resolution, an SN ratio is decreased. As a result, image quality or accuracy of the calculation image is decreased.

The present invention is provided in view of the forgoing and is to provide a technology of improving image quality of a calculation image or parameter estimation accuracy even in a case of using a method of simultaneously generating calculation images of a plurality of parameters.

Solution to Problem

In the present invention, by utilization of a reconstructed image in an optimal resolution of each parameter to be estimated, a value of the parameter is estimated and a calculation image that is a distribution of the value of the parameter is acquired. A reconstructed image in an optimal resolution is acquired by adjustment of a resolution of a reconstructed image acquired with an estimation parameter with the highest optimal resolution among parameters to be estimated in scanning. Alternatively, in scanning, only a reconstructed image used for calculation of a predetermined parameter to be estimated is acquired in an optimal resolution of the parameter to be estimated.

Advantageous Effects of Invention

According to the present invention, it is possible to improve image quality of a calculation image or parameter estimation accuracy even in a case of simultaneously generating calculation images of a plurality of parameters.

BRIEF DESCRIPTION OF DRAWINGS

FIG. 4(a) is a view for describing a pulse sequence of the first embodiment and FIG. 4(b) is a view for describing a k-space by the pulse sequence of the first embodiment.

FIG. 10(a) to FIG. 10(d) are views for describing a parameter distribution acquired by a method of the first embodiment and a parameter distribution acquired by the conventional method.

FIG. 11(a) is a view for describing a single echo sequence of a second embodiment and FIG. 11(b) is a view for describing a multi echo sequence of the second embodiment.

FIG. 14(a) is a view for describing a pulse sequence of a modification example of the present invention and FIG. 14(b) is a view for describing a k-space by the pulse sequence in FIG. 14(a).

DESCRIPTION OF EMBODIMENTS

First Embodiment

In the following, a first embodiment to which the present invention is applied will be described. In the following, in all drawings for a description of embodiments of the present invention, the same reference sign is assigned to those basically including the same function and a repeated description thereof is omitted.

Figure 1:
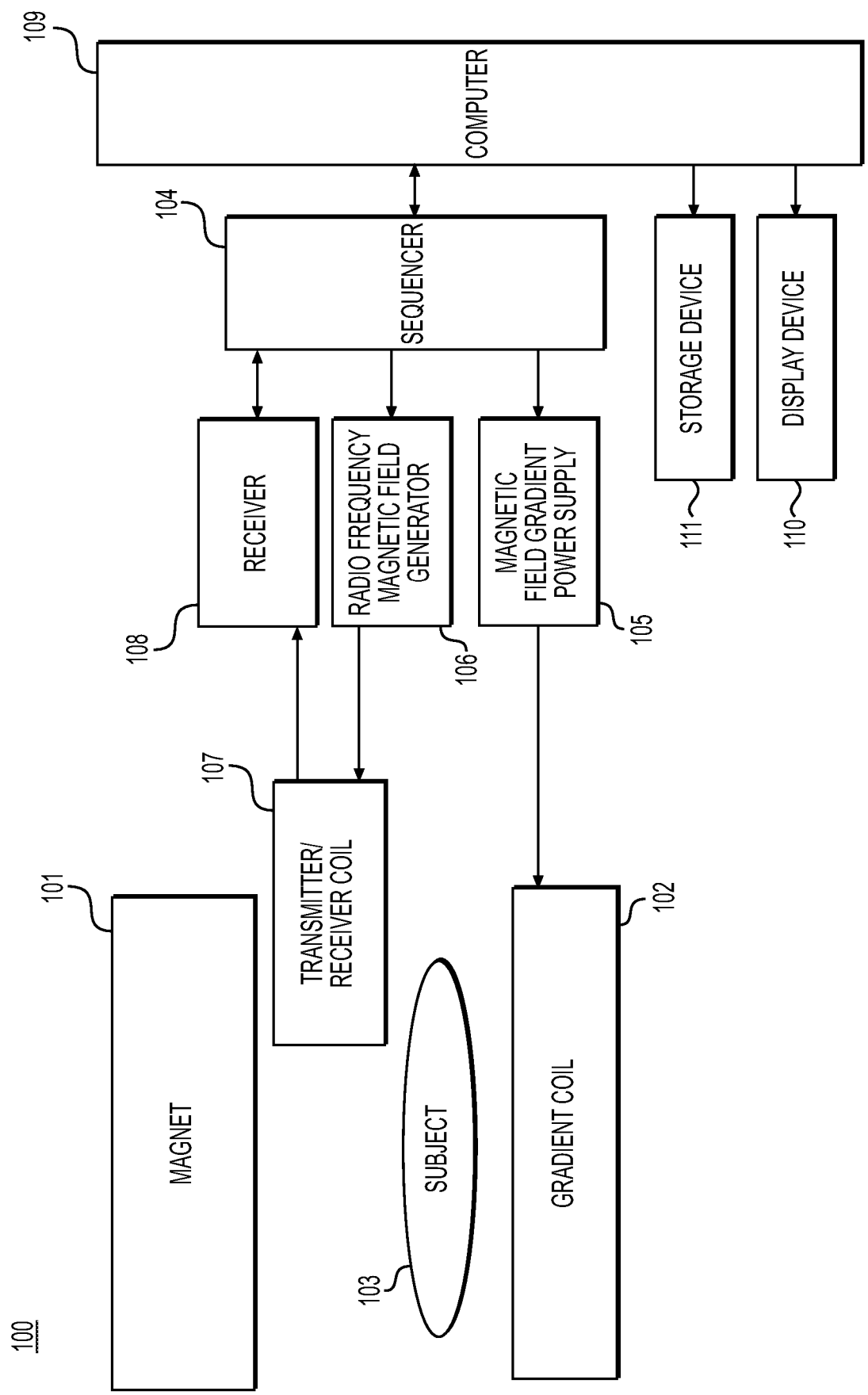
FIG. 1 is a block diagram illustrating a schematic configuration of an MRI apparatus of a first embodiment.

First, an MRI apparatus of the present embodiment will be described. FIG. 1 is a block diagram illustrating a schematic configuration of an MRI apparatus 100 of the present embodiment. The MRI apparatus 100 includes a magnet 101 that generates a static magnetic field, a gradient coil 102 that generates a magnetic field gradient, a sequencer 104, a magnetic field gradient power supply 105, a radio frequency magnetic field generator 106, a transmitter/receiver coil 107 that irradiates a radio frequency magnetic field and detects a nuclear magnetic resonance signal, a receiver 108, a computer 109, a display device 110, and a storage device 111. Single transmitter/receiver coil 107 is illustrated in the drawing. However, a transmitter coil and a receiver coil may be included separately.

A subject (such as living body) 103 is placed on a bed (table) or the like and arranged in a static magnetic field space generated by the magnet 101.

The sequencer 104 gives a command to each of the magnetic field gradient power supply 105 and the radio frequency magnetic field generator 106 to generate a magnetic field gradient and a radio frequency magnetic field. The radio frequency magnetic field is applied to the subject 103 through the transmitter/receiver coil 107. A nuclear magnetic resonance signal (NMR signal; echo signal) generated from the subject 103 is received by the transmitter/receiver coil 107 and is detected by the receiver 108.

A nuclear magnetic resonance frequency (detection reference frequency; resonance frequency $f_0$) that is a reference of the detection is set by the sequencer 104. The detected echo signal is transmitted to the computer 109 and signal processing such as image reconstruction is performed therein. A result of this is displayed on the display device 110. When necessary, the storage device 111 may store a detected signal or a measurement condition.

The sequencer 104 generally performs control in such a manner that each device operates at timing and in strength that are previously programmed. A program that specifically describes a radio frequency magnetic field, a magnetic field gradient, or timing or strength of receiving a signal is referred to as a pulse sequence (pulse sequence).

The computer 109 operates each unit according to the pulse sequence and measures an echo signal. Also, various kinds of signal processing are performed on the acquired echo signal and an intended image is acquired. Note that measurement of an echo signal is performed by the sequencer 104.

The computer 109 includes a CPU and a memory. Then, each function realized by the computer 109 is realized when the CPU of the computer 109 loads a program stored in the storage device 111 into the memory and executes the program. Also, a part or a whole of the function may be realized by hardware such as an application specific integrated circuit (ASIC) or a field-programmable gate array (FPGA). Also, various kinds of data used for processing of each function and various kinds of data generated in the processing are stored into the storage device 111.

Note that the magnet 101 functions as a static magnetic field generating unit. The gradient coil 102 and the magnetic field gradient power supply 105 function as a magnetic field gradient generation unit. The transmitter/receiver coil 107 and the radio frequency magnetic field generator 106 function as a radio frequency transmitting unit. The transmitter/receiver coil 107 and the receiver 108 function as a receiver unit. The sequencer 104 and the computer 109 function as a control unit. The computer 109 also functions as an image reconstruction unit.

Figure 2:
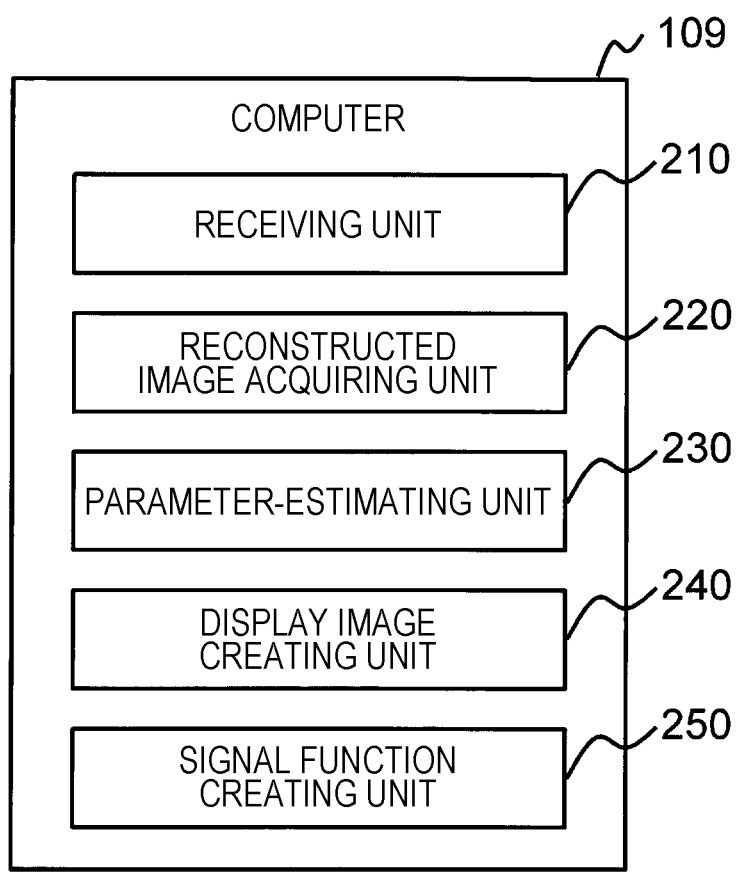
FIG. 2 is a functional block diagram of a computer of the first embodiment.

In the present embodiment, a calculation image of a subject parameter and/or an apparatus parameter is acquired in an optimal resolution from a plurality of reconstructed images acquired by different scan parameters. In order to realize this, as illustrated in FIG. 2, the computer 109 of the present embodiment includes a receiving unit 210, a reconstructed image acquiring unit 220, a parameter-estimating unit 230, and a display image creating unit 240. Also, as described later, when it is necessary to create a signal function, a signal function creating unit 250 is further included.

In the following, in the present embodiment, a parameter that can be arbitrarily set by a user during execution of a pulse sequence will be referred to as a scan parameter and a parameter that depends on the subject 103 will be referred to as a subject parameter. In addition, a parameter unique for an MRI apparatus will be referred to as an apparatus parameter.

As the scan parameter, for example, there is repetition time (TR), echo time (TE), strength of a radio frequency magnetic field (flip angle (FA)), or a phase of a radio frequency magnetic field (θ). Also, as the subject parameter, there is longitudinal relaxation time (T1), transverse relaxation time (T2), spin density (ρ), a resonance frequency difference ($\Delta f_0$), a diffusion coefficient (D), a strength of a radio frequency magnetic field (irradiation strength distribution of radio frequency magnetic field; $B_1$), or the like. Moreover, as the apparatus parameter, there is static magnetic field strength ($B_0$), a sensitivity distribution of a receiver coil ($S_c$), or the like. Note that the resonance frequency difference $\Delta f_0$ is a difference between a resonance frequency and a reference frequency $f_0$ of each pixel.

[Receiving Unit]

The receiving unit 210 receives an instruction from a user. The receiving unit 210 receives necessary information in execution of scanning by the reconstructed image acquiring unit 220. Moreover, in the present embodiment, designation of a subject parameter and/or an apparatus parameter to be an object of creating a calculation image (parameter distribution) (estimation parameter) and designation of a scan parameter set used for scanning are received. These pieces of information are received through a receiving screen displayed on the display device 110. Also, information of a parameter that can be designated is previously held in the storage device 111.

[Reconstructed Image Acquiring Unit]

The reconstructed image acquiring unit 220 of the present embodiment executes scanning by using a previously-set scan parameter according to a predetermined pulse sequence and acquires a reconstructed image. An instruction is given to the sequencer 104 in such a manner that each part is controlled according to a scan parameter and a pulse sequence, whereby the scanning is executed.

In the present embodiment, scanning is performed according to a predetermined pulse sequence by utilization of a plurality of scan parameter sets in which values of one or more scan parameters are different, whereby a reconstructed image is acquired for each scan parameter set.

Here, the reconstructed image acquiring unit 220 of the present embodiment scans according to a scanning condition corresponding to each estimation parameter received by the receiving unit 210 and acquires a reconstructed image. Note that the scanning condition corresponding to each estimation parameter includes an optimal resolution of the estimation parameter and is previously held in the storage device 111 or the like.

[Parameter-Estimating Unit]

By using a plurality of reconstructed images and a signal function of a pulse sequence that is followed in acquisition of the reconstructed images, the parameter-estimating unit 230 estimates a value of a parameter that is at least one of a subject parameter depending on the subject 103 and an apparatus parameter depending on an apparatus and that is a parameter to be estimated (estimation parameter). In the present embodiment, a value of an estimation parameter is estimated by utilization of a reconstructed image in an optimal resolution for each estimation parameter.

The estimation of a value of the estimation parameter is performed for each pixel. Thus, the parameter-estimating unit 230 of the present embodiment outputs, as a result, a parameter distribution that is a parameter value of each pixel. A detail of the parameter estimation processing performed by the parameter-estimating unit 230 of the present embodiment will be described later.

[Display Image Creating Unit]

The display image creating unit 240 generates a display image from a parameter distribution generated by the parameter-estimating unit 230 and displays the image on the display device 110. Note that the display image creating unit 240 may not be included.

Figure 3:
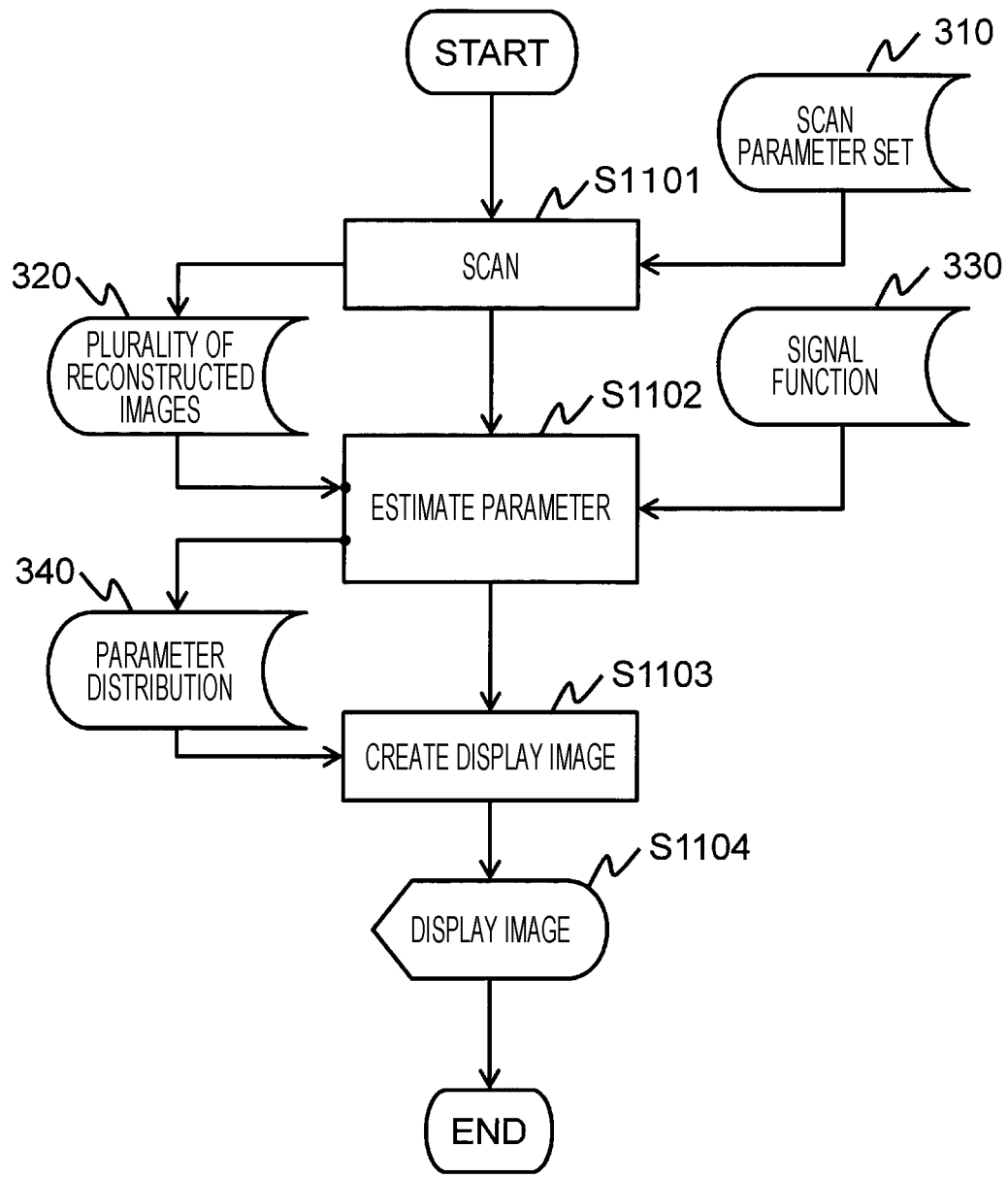
FIG. 3 is a flowchart of calculation image creating processing of the first embodiment.

First, an outline of a flow of calculation image creating processing performed by these units is illustrated in FIG. 3.

First, according to a predetermined pulse sequence, the reconstructed image acquiring unit 220 scans and acquires a plurality of reconstructed images 320 (step S1101). Here, as described above, in the present embodiment, scanning is performed by utilization of a plurality of scan parameter sets 310 in which values of one or more scan parameters are different. Then, the parameter-estimating unit 230 performs parameter estimation processing by using the signal function 330 and the plurality of reconstructed images 320 (step S1102) and acquires a parameter value (parameter distribution) 340 of each pixel of an intended estimation parameter. Then, the display image creating unit 240 creates a display image (step S1103), displays the image on the display device 110 (step S1104), and ends the processing.

[Parameter Estimation Processing]

In the following, parameter estimation processing of the present embodiment will be described.

As described above, the parameter-estimating unit 230 uses the signal function 330 in the parameter estimation. Before a description of the parameter estimation processing, the signal function 330 will be described.

The signal function 330 is a function that determines a relationship between each pixel value of a reconstructed image and scan parameters, subject parameters, and apparatus parameters in each pulse sequence. Generally, the function is analytically calculated for each pulse sequence and is formulated. When a pulse sequence including a formulated signal function is used in the parameter estimation, the signal function 330 is used.

On the other hand, in a case where a pulse sequence in which a signal function is not formulated, the signal function creating unit 250 previously creates the signal function 330 in the present embodiment. That is, the signal function creating unit 250 of the present embodiment creates the signal function 330 by numerical simulation in a case where a pulse sequence used in creation of a calculation image is a sequence in which a signal function cannot be calculated analytically or a sequence in which a signal function is not known yet. Note that in a case where a pulse sequence in which a signal function can be calculated analytically or a sequence in which a signal function is already known is used, the signal function creating unit 250 may not be included.

[Pulse Sequence]

Before a description of a detail of signal function creating processing performed by the signal function creating unit 250, an example of pulse sequence in which a signal function is not calculated analytically will be described. Here, an RF-spoiled GE sequence will be described as an example of the pulse sequence.

FIG. 4(a) is a timing chart of an RF-spoiled GE sequence 610. RF, Gs, Gp, and Gr respectively indicate timing of applying a radio frequency magnetic field (RF) pulse, a slice selecting magnetic field gradient pulse, a phase encoding magnetic field gradient pulse, and a readout magnetic field gradient pulse. In the following, similar application is performed in the present description.

In the RF-spoiled GE sequence 610, first, a radio frequency magnetic field (RF) pulse 612 is emitted along with application of a slice magnetic field gradient pulse 611 and a magnetization of a predetermined slice in an object body is excited. Then, a slice rephasing magnetic field gradient pulse 613, a phase encoding magnetic field gradient pulse 614 for addition of positional information in a phase encoding direction to a phase of a magnetization, and readout magnetic field gradient for dephasing 615 are applied. Then, during application of a readout magnetic field gradient pulse 616 for addition of positional information in a readout direction, a magnetic resonance signal (echo signal) 617 is measured. Then, finally, a phase encoding magnetic field gradient pulse for dephasing 619 is applied.

In a case where scanning is performed by utilization of the RF-spoiled GE sequence 610, the reconstructed image acquiring unit 220 repeatedly performs the above procedure in repetition time TR while changing strength (amount of phase encoding kp) of the phase encoding magnetic field gradient pulse 614 and the phase encoding magnetic field gradient pulse for dephasing 619 and changing an incrementation value of a phase of the RF pulse 612 by 117° and measures echoes necessary for acquiring one image. Note that here, a phase θ (n) of an nth applied RF pulse 612 becomes θ (n-1)+117n.

Accordingly, as illustrated in FIG. 4(b), each echo signal is arranged in a k-space. Then, the reconstructed image acquiring unit 220 reconstructs an image by the two-dimensional inverse Fourier transform. Note that when the RF-spoiled GE sequence 610 is used, a reconstructed image in which longitudinal relaxation time (T1) is weighted is acquired.

[Signal Function Creating Processing]

In the following, processing of creating a signal function of the RF-spoiled GE sequence 610 which processing is performed by the signal function creating unit 250 will be described.

Figure 5:
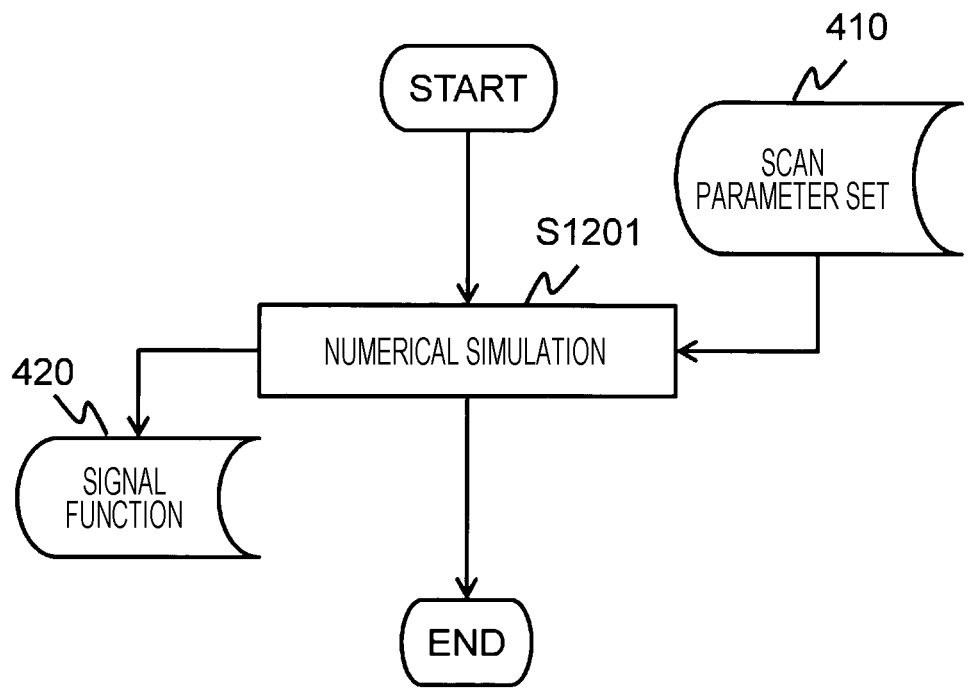
FIG. 5 is a flowchart of signal function creating processing of the first embodiment.

As illustrated in FIG. 5, the signal function creating unit 250 performs numerical simulation by using a plurality of scan parameter sets 410 in which values of one or more scan parameters are different (step S1201) and generates a signal function 420. The plurality of scan parameter sets 410 is a combination of the plurality of different scan parameters and subject parameters.

[Signal Function]

A signal function $f_s$ of the RF-spoiled GE sequence 610 is expressed by the following equation (1) with longitudinal relaxation time T1, transverse relaxation time T2, spin density ρ, and radio frequency magnetic field strength $B_1$ of subject parameters, a receiver coil sensitivity $S_c$ of an apparatus parameter, and a flip angle FA, repetition time TR, echo time TE, and an RF phase image value θ of scan parameters that can be changed in the RF-spoiled GE sequence 610.

[Math 1]

$$I=f_s(\rho,T1,T2,B_1,FA,TR,TE,\theta,S_c)=\rho S_c f(T1,T2,B_1\times FA,\theta,TR,TE) \quad (1)$$

Note that since being a coefficient of FA in scanning, $B_1$ is multiplied by FA. Also, since functioning as proportionality coefficients with respect to signal strength, ρ and $S_c$ are on the outside of a function.

[Scan Parameter Set]

The signal function creating unit 250 of the present embodiment comprehensively changes the scan parameters FA, TR, and TE with respect to arbitrary values of T1 and T2 of the subject parameters and acquires a signal in numerical simulation. Then, the signal function creating unit 250 performs interpolation of the acquired signal and creates a signal function.

Note that as described above, in the RF-spoiled GE sequence 610, a changeable scan parameters are FA, TR, TE, and θ. However, the RF phase incrementation value θ among these is fixed to 117°. θ is fixed in order to acquire image contrast with low T2 dependence equivalent to that of FLASH which is one of a high-speed scanning method. When θ is changed, T2 dependence of the image contrast changes greatly.

Here, it is assumed that the spin density ρ, $B_1$, and $S_c$ of an object of scanning are constant (1, for example).

An example of values of subject parameters T1 and T2 used in creation of a signal function and values of changed scan parameters FA, TR, and θ are described in the following. A range of a scan parameter used in actual scanning and a range of T1 and T2 of a subject are included.

T1 (15) [s]: 0.05, 0.07, 0.1, 0.14, 0.19, 0.27, 0.38, 0.53, 0.74, 1.0, 1.5, 2.0, 2.8, 4.0, and 5.6

T2 (17) [s]: 0.01, 0.02, 0.03, 0.04, 0.05, 0.07, 0.1, 0.14, 0.19, 0.27, 0.38, 0.53, 0.74, 1.0, 1.4, 2.0, and 2.8

TR (4) [ms]: 10, 20, 30, and 40

FA (10) [deg.]: 5, 10, 15, 20, 25, 30, 35, 40, 50, and 60

θ (17) [deg.]: 0, 1, 2, 3, 4, 5, 6, 7, 8, 9, 10, 12, 14, 16, 18, 20, and 22

In this case, the signal function creating unit 250 generates 173400 scan parameter sets 410 of all combinations of the above scan parameters and subject parameters and calculates a signal value by each of the scan parameter sets 410 by the numerical simulation.

[Numerical Simulation]

In the numerical simulation, a Bloch equation that is a fundamental equation of a magnetic resonance phenomenon is solved with a subject model in which spins are arranged on a grid point, a pulse sequence, scan parameters, and apparatus parameters as input and magnetic resonance signals are output.

The subject model is given as a spatial distribution of spins (γ, M0, T1, T2, and Cs). Here, γ is a gyromagnetic ratio, M0 is a thermal equilibrium magnetization (spin density), and T1 and T2 are respectively longitudinal relaxation time and transverse relaxation time.

The Bloch equation is a first order linear differential equation and is expressed by the following equation.

[Math 2]

$$\frac{d}{dt}\begin{pmatrix}M_x\\M_y\\M_z\end{pmatrix}=\begin{pmatrix}-1/T2 & \gamma H & \\ -\gamma H & -1/T2 & \gamma H1 \\ & -\gamma H1 & -1/T1\end{pmatrix}\begin{pmatrix}M_x\\M_y\\M_z\end{pmatrix}+\begin{pmatrix}0\\0\\M_0/T1\end{pmatrix} \quad (2)$$

$$H = B_0 + G_x x + G_y y + G_z z + 2\pi f_0/\gamma$$

Here, (x, y, z) indicates a three-dimensional orthogonal coordinate system and z is equal to a direction of a static magnetic field (strength is $B_0$). Also, (Mx, My, Mz) is a spin, $G_x$, $G_y$, and $G_z$ are magnetic field gradient strength respectively in directions of subscripts, H1 is radio frequency magnetic field strength, and $f_0$ is a frequency of a rotating coordinate system.

[Interpolation]

When a signal value of each of the scan parameter sets 410 is acquired by the above equation (2), the signal function creating unit 250 performs interpolation thereof and creates a signal function $f_s$ (420). As the interpolation, first to third linear interpolation or spline interpolation can be used.

Figure 6:
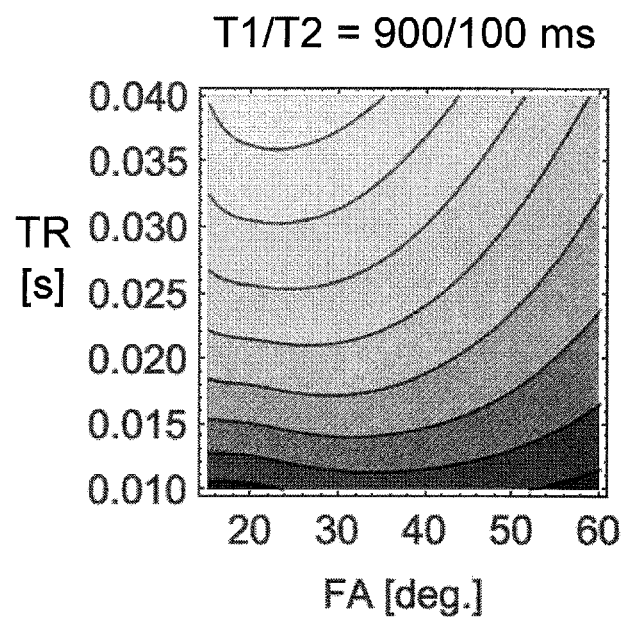
FIG. 6 is a view for describing an example of a strength distribution of a signal function of the first embodiment.

A part of strength of the signal function 420 created by the signal function creating unit 250 of the present embodiment by the above method is illustrated in FIG. 6. Here, strength of each value of FA and TR in a case where T1 is 900 ms, T2 is 100 ms, and θ is 5° is illustrated. A horizontal axis is FA [deg.] and a vertical axis is TR [s]. The stronger signal strength is, the heavier the color is.

[Parameter Estimation Processing]

Next, a detail of parameter estimation processing performed by the parameter-estimating unit 230 of the present embodiment will be described. As described above, in the present embodiment, a value of an estimation parameter is estimated by utilization of a reconstructed image in an optimal resolution of each estimation parameter. As described above, an optimal resolution of each estimation parameter is previously held in the storage device 111 or the like.

In the estimation, the parameter-estimating unit 230 uses a plurality of reconstructed images 320 and a signal function 330 of a pulse sequence. The reconstructed image acquiring unit 220 performs imaging by using a plurality of scan parameter sets 310 according to a predetermined pulse sequence, whereby the plurality of reconstructed images 320 is acquired. The plurality of scan parameter sets may include having the same scan parameter.

Here, the number of acquired reconstructed images 320 is equal to or larger than the number of estimation parameters to be estimated. Also, the plurality of acquired reconstructed images 320 is acquired in a resolution of an estimation parameter with the highest optimal resolution among estimation parameters to be estimated (highest resolution).

For example, as described above, in a case of estimating T1, T2, and $B_1$ of the subject parameters and $\rho S_c$ that is a product of $\rho$ and the apparatus parameter $S_c$, $B_1$ does not need a high resolution compared to T1 and T2 because of its spatial smooth change. Thus, in this case, an image in a resolution necessary for estimation of T1 and T2 is acquired.

Note that the resolution is determined by an imaging field of view FOV and the number of encoding steps. These scan parameters are set through the receiving unit 210.

Also, with respect to an estimation parameter with an optimal resolution lower than the highest resolution, the parameter-estimating unit 230 reduces a resolution of a reconstructed image acquired by the reconstructed image acquiring unit 220 into the optimal resolution of the estimation parameter and estimates a value of the estimation parameter.

Here, the parameter-estimating unit 230 serially estimates values of the estimation parameters starting from an estimation parameter with a low optimal resolution. In the estimation, an already-estimated value of an estimation parameter is adjusted to an optimal resolution of an estimation parameter to be estimated and is used along with the signal function 330.

Figure 7:
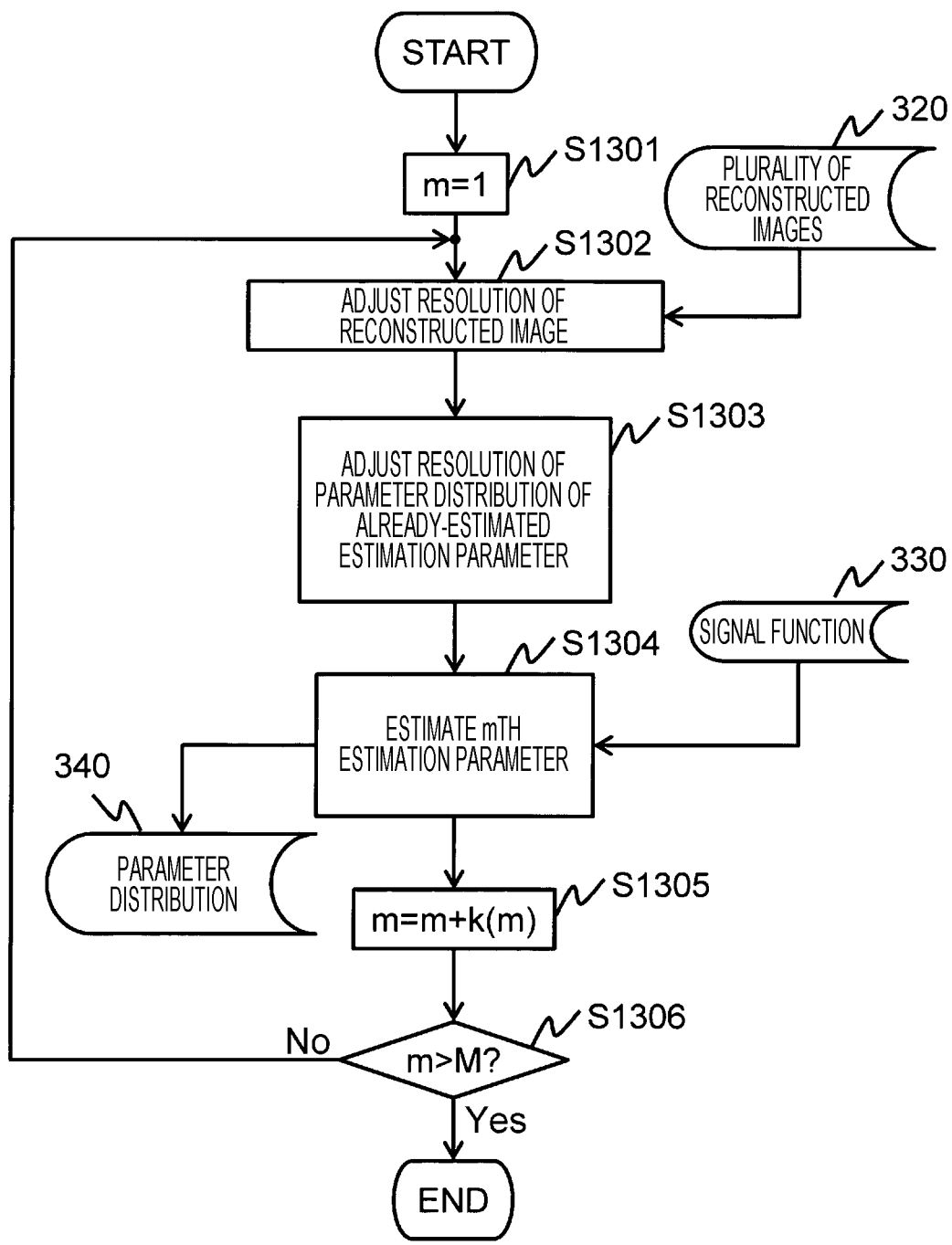
FIG. 7 is a flowchart of parameter estimation processing of the first embodiment.
Figure 8:
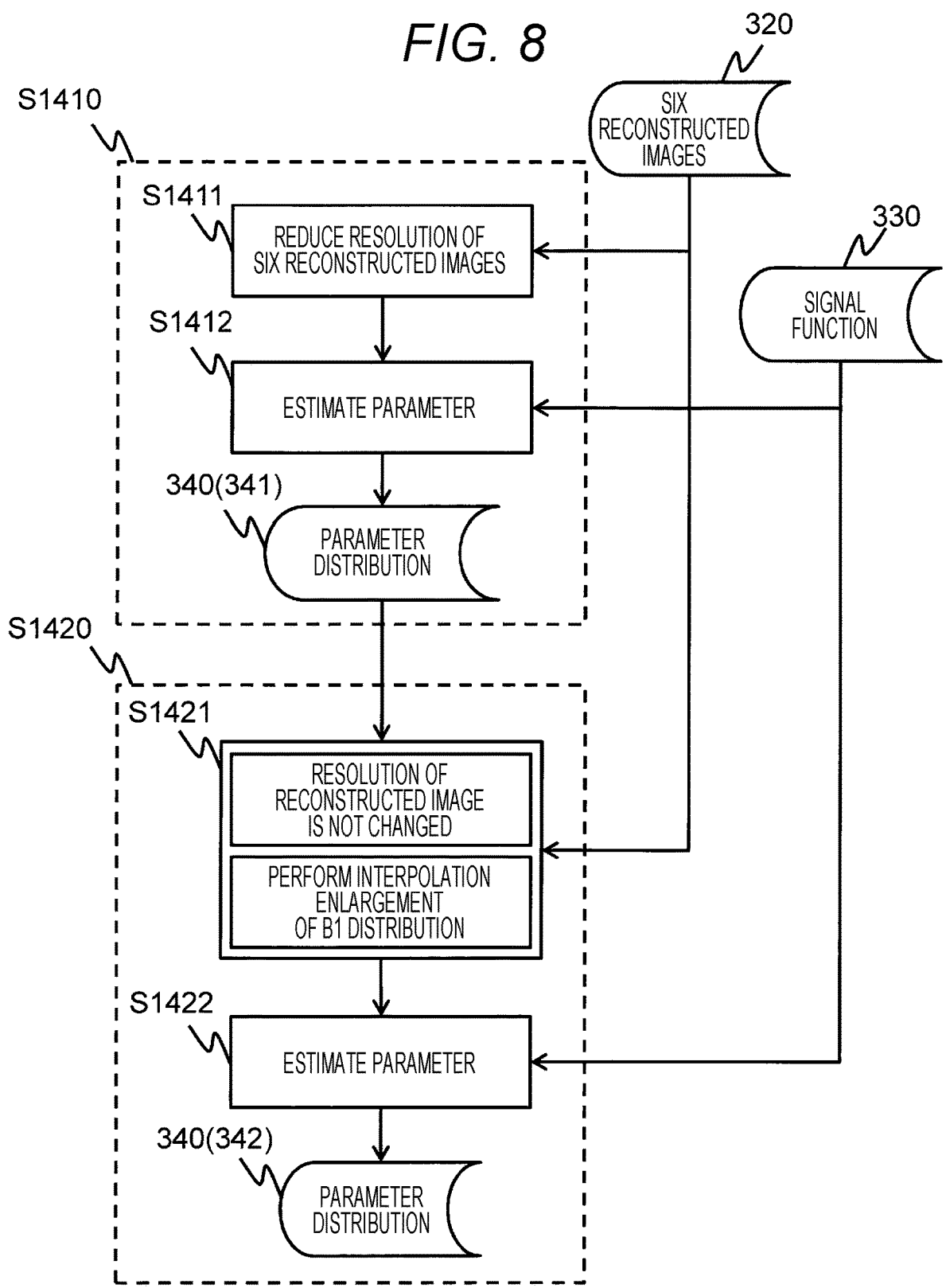
FIG. 8 is a view for describing a detail example of the parameter estimation processing of the first embodiment.

In the following, a detail of the parameter estimation processing performed by the parameter-estimating unit 230 of the present embodiment will be described along a flow of the processing. FIG. 7 is a processing flow of the parameter estimation processing of the present embodiment. Here, it is assumed that the number of estimation parameters is M (M is integer equal to or larger than 2).

In this case, a plurality of scan parameter sets (FA, TR, and θ) 310 is previously prepared. In step S1101 described above, the reconstructed image acquiring unit 220 acquires the reconstructed images 320 the number of which is equal to that of the prepared scan parameter sets 310.

It is generally necessary that the number of prepared scan parameter sets 310 is equal to or larger than M that is the number of estimation parameters. This is because the number of equations (scan parameter set and image scanned thereby) needs to be equal to or larger than unknown quantity (estimation parameter) in calculation of solutions of the equations. Here, for example, it is assumed that N sets (N is integer equal to or larger than M) are prepared. Thus, the number of reconstructed images 320 is also N.

For example, when the number of estimation parameters is four (T1, T2, $B_1$, and a), the number of scan parameter sets 310 is larger than four and is, for example, six. Note that estimation accuracy is improved by an increase in the number of scan parameter sets. However, time for scanning is increased. Also, here, a plurality of reconstructed images 320 is acquired in a resolution of an estimation parameter, which needs the highest resolution, among estimation parameters to be estimated.

The parameter-estimating unit 230 estimates M estimation parameters. In the present embodiment, estimation is serially performed in order from an estimation parameter with a low optimal resolution (step S1301). Also, estimation parameters with the same optimal resolution are estimated simultaneously. In the following, it is assumed that the number of estimation parameters with the mth lowest optimal resolution is k (m).

First, the N reconstructed images 320 are adjusted to the optimal resolution of the k (m) estimation parameters with the mth lowest optimal resolution (step S1302). Here, resolutions of the N reconstructed images 320 are reduced. Reduction of resolution is performed, for example, by adding of values of a plurality of pixels.

Note that in the reduction of resolution, a degree of the resolution is determined according to an SN ratio of the reconstructed images 320 and an optimal resolution of the estimation parameters to be estimated. That is, when the SN ratio of the reconstructed images 320 is adequately high, the resolution can be determined arbitrarily. However, when the SN ratio is low, resolution is made as low as possible according to a distribution of the estimation parameters. Accordingly, it is possible to keep the parameter estimation accuracy as high as possible even when the SN ratio is low.

A resolution of a parameter distribution of an already-estimated estimation parameter is adjusted to the resolution of the images which resolution is adjusted in step S1302 (step S1303). Here, since a resolution of a parameter distribution of the previously-estimated estimation parameter is equal to or lower than an estimation parameter that is currently estimated, interpolation enlargement processing is performed and the resolution is adjusted. As the interpolation enlargement, for example, the sum of homogeneous functions, which are lower than a predetermined degree n, expressed in the following expression (3) is used. For example, the degree n is preferably around 6.

[Math 3]

$$\sum_{p+q+r \leq n} a_{pqr} x^p y^q z^r \quad (3)$$

Then, a parameter to be estimated is estimated by utilization of an image in the resolution acquired in step S1302, a parameter distribution, in which the resolution is already adjusted, of the already-estimated estimation parameter, and the previously-created signal function 330 (step S1304). As a result, a parameter distribution 340 of the estimation parameter is acquired.

More specifically, a signal value I of each pixel is fitted to a function f in the following equation (4) that is modified from the equation (1). Thus, an estimation parameter is estimated.

[Math 4]

$$I = af(T1, T2, \theta, B_1 \times FA, TR)$$

$$a = \rho S_c \qquad (4)$$

Note that function fitting is performed by a least squares method expressed by the following equation (5).

[Math 5]

$$x^2 = \sum_{FA,\theta,TR} \{I(FA, \theta, TR) - af(T1, T2, \theta, B_1 \times FA, TR)\} = \min \qquad (5)$$

Here, x is the sum of residuals of pixel values of a signal function and a phantom and I is a pixel value in (FA, θ, and TR).

The above processing is repeatedly performed with respect to all of the estimation parameters (step S1305 and S1306) and the processing is ended.

Example

In the following, parameter estimation processing performed by the parameter-estimating unit 230 with respect to parameters of the above-mentioned present embodiment will be described in a detailed example with reference to FIG. 8, and FIG. 9(a) to FIG. 9(f).

Here, it is assumed that there are four estimation parameters ($B_1$, a, T1, and T2). Thus, the number of prepared scan parameter sets 310 is larger than that and is six. The scan parameter sets 310 are respectively referred to as P1 to P6.

The scan parameter sets 310 from P1 to P6 are six sets among twelve imaging parameter sets acquired by combinations of FA being 10° and 30°, θ being 2°, 6°, and 20°, and TR being 10 ms and 40 ms. Note that TE is fixed to 5 ms. Note that as the scan parameter sets 310, for example, sets with which accurate estimation is possible are selected according to propagation of error or the like.

Also, it is assumed that only $B_1$ among the estimation parameters to be estimated has an optimal resolution lower than those of the other estimation parameters. That is, in this example, an estimation parameter with the lowest optimal resolution is $B_1$ only. Also, there are three estimation parameters with the second lowest optimal resolution which parameters are a, T1, and T2.

Thus, first, the reconstructed image acquiring unit 220 acquires six reconstructed images 320 in an optimal resolution of a, T1, and T2. An example of the six reconstructed images 320 which images are acquired by the reconstructed image acquiring unit 220 by utilization of each of the scan parameter sets 310 is illustrated in FIG. 9(a).

First, the parameter-estimating unit 230 estimates a parameter value of $B_1$ ($B_1$ distribution) (step S1410). Here, a resolution of the images is reduced according to the optimal resolution of $B_1$ and estimation is performed.

In the estimation of the $B_1$ distribution, first, resolutions of the six reconstructed images 320 are reduced to the optimal resolution of the estimation parameter $B_1$ (step S1401).

Figure 9:
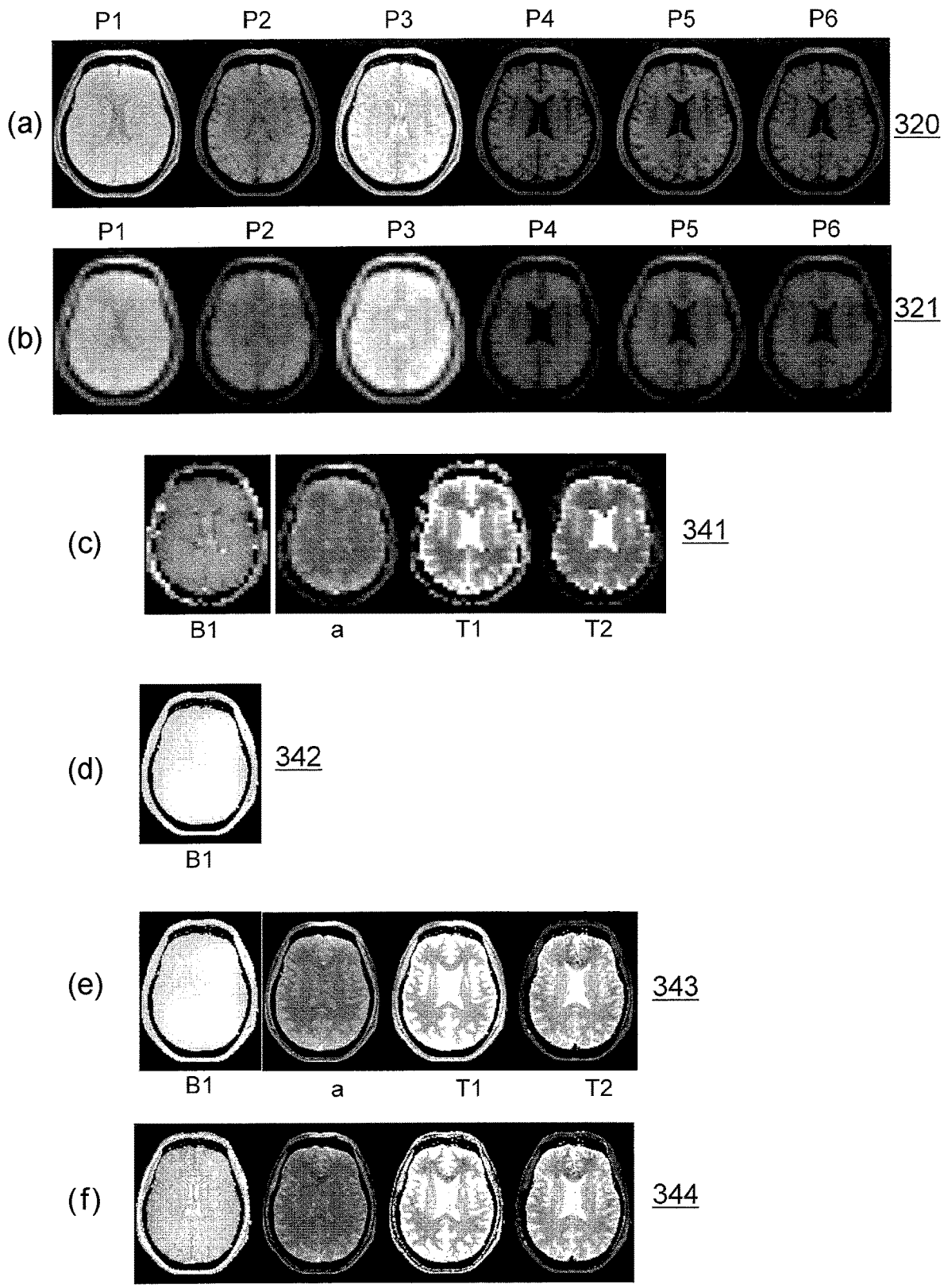
FIG. 9(a) is a view for describing an example of a reconstructed image that is initially acquired in the processing illustrated in FIG. 8, FIG. 9(b) to FIG. 9(e) are views for describing examples of a reconstructed image or a parameter distribution acquired in the middle of the processing illustrated in FIG. 8.
FIG. 9(f) is a view for describing an example of a parameter distribution acquired by a conventional method.

Images 321 that are the reconstructed images 320, which are illustrated in FIG. 9(a) and resolutions of which are reduced, are illustrated in FIG. 9(b).

The images 321 illustrated in FIG. 9(b) are created by addition of 4×4 pixels of the original reconstructed images 320 into one pixel. For example, in a case where the resolution of the original reconstructed images 320 is 1.6 mm×1.6 mm, 4×4 pixels are added to be one pixel of 6.4 mm×6.4 mm and the images 321 are acquired.

Then, by utilization of the signal function 330 and the six images 321 with the reduced resolution, a parameter value of $B_1$ in each pixel is estimated (step S1402) and a parameter distribution ($B_1$ distribution) 341 is acquired. Note that here, a, T1, and T2 are estimated in the resolution identical to that of $B_1$. An estimation result 341 of these is illustrated in FIG. 9(c).

Next, the parameter-estimating unit 230 estimates the remaining estimation parameters (T1, T2, and a) (step S1420). Here, a $B_1$ distribution, on which interpolation enlargement is performed, and a plurality of reconstructed images 320 in the resolution at the time of acquisition are used.

Thus, first, interpolation enlargement of the $B_1$ distribution 341 is performed and a resolution thereof is made identical to that of the six original reconstructed images 320 (step S1421). A $B_1$ distribution 342 on which the interpolation enlargement is performed is illustrated in FIG. 9(d).

Then, by utilization of the original reconstructed images 320 illustrated in FIG. 9(a), the $B_1$ distribution 342 after the interpolation enlargement, and the signal function 330, three parameters of a, T1, and T2, are estimated in the resolution of the original reconstructed images 320 (step S1402) and a parameter distribution is acquired. The $B_1$ distribution 342 on which the interpolation enlargement is performed and a parameter distribution 343 of each of the estimated a, T1, and T2 are illustrated in FIG. 9(e).

Note that in the estimation processing in step S1402, since the $B_1$ distribution 342 on which the interpolation enlargement is performed is used as a correct value, $B_1$ is known. There are three kinds of unknown quantity which are a, T1, and T2. Since the number of kinds of unknown quantity is decreased, processing speed is increased and estimation accuracy is improved.

Here, a result in a case where distributions of all estimation parameters ($B_1$, a, T1, and T2) are acquired from reconstructed images acquired by the conventional method, that is, in a resolution corresponding to an estimation parameter with the highest optimal resolution (parameter distribution) 344 is illustrated in FIG. 9(f).

When the parameter distribution 343 illustrated in FIG. 9(e) and the parameter distribution 344 illustrated in FIG. 9(f) are compared with each other, it is understood that a noise in the result 343 by the method of the present embodiment is decreased from that by the conventional method.

In order to indicate an effect more clearly, profiles 513 and 523 of one line in a vertical direction (line of an approximate center position in the horizontal direction) of the $B_1$ distribution and the a distribution 343 in FIG. 9(e) are respectively illustrated in FIG. 10(a) and FIG. 10(b). Also, profiles 514 and 524 of the $B_1$ distribution and the a distribution 344 in FIG. 9(f) are respectively illustrated in FIG. 10(c) and FIG. 10(d). Note that in the present drawings, a horizontal axis indicates a position on one line and a vertical axis indicates a signal strength.

As illustrated in the present drawings, when the profile 513 by the method of the present embodiment and the profile 514 by the conventional method are compared with each other with respect to the $B_1$ distribution, it is understood that there is hardly a noise in the distribution by the method of the present embodiment because of interpolation enlargement. With respect to the a distribution, when the profile 523 by the method of the present embodiment and the profile 524 by the conventional method are compared with each other, it is understood that there is less noise in the distribution acquired by the method of the present embodiment.

As described above, the MRI apparatus 100 of the present embodiment includes the parameter-estimating unit 230 configured to estimate a value of an estimation parameter of at least one of subject parameters depending on the subject 103 and apparatus parameters depending on an apparatus by using the plurality of reconstructed images 320 and the signal function 330 of the pulse sequence which is followed in acquisition of the reconstructed images 320. The plurality of reconstructed images 320 is acquired by imaging performed according to the pulse sequence by utilization of the plurality of scan parameter sets 310. The signal function 330 is a function that defines, for each pulse sequence, a relationship between each pixel value of the reconstructed images and the scan parameters, the subject parameters, and the apparatus parameters. The parameter-estimating unit 230 estimates the values by using the reconstructed images in an optimal resolution of each of the estimation parameters.

In such a manner, according to the present embodiment, a value of a parameter to be estimated is estimated by utilization of images in an optimal resolution thereof. Thus, it is possible to acquire a calculation image accurately at high speed without a decrease in the SN ratio.

Also, the plurality of reconstructed images 320 may have the highest resolution that is an optimal resolution of an estimation parameter with the highest optimal resolution among the estimation parameters. With respect to an estimation parameter with an optimal resolution lower than the highest resolution, the parameter-estimating unit 230 may reduce the resolution of the reconstructed images 320 to the optimal resolution of the estimation parameter and estimate the value. Here, the parameter-estimating unit 230 may serially estimate the value starting from an estimation parameter with low optimal resolution. In the estimation, the parameter-estimating unit 230 may adjust a value of an already-estimated estimation parameter to an optimal resolution of an estimation parameter to be estimated and may use the value along with the signal function 330.

Thus, according to the present embodiment, estimation is started from an estimation parameter with a low optimal resolution which parameter needs the small number of calculations. The number of unknown parameters to be estimated is decreased as an optimal resolution becomes higher. Thus, divergence or the like during the processing is decreased and an accurate estimation result can be acquired.

Second Embodiment

Next, the second embodiment of the present invention will be described. In the first embodiment, an image is acquired in a resolution corresponding to that of an calculation image of an estimation parameter with the highest optimal resolution and the resolution is decreased to an optimal resolution in estimation of a parameter value. On the other hand, in the present embodiment, in a case where a contributed reconstructed image is known with respect to each estimation parameter, the reconstructed image is acquired in an optimal resolution in acquisition of the reconstructed image.

An MRI apparatus of the present embodiment basically includes a configuration similar to that of the MRI apparatus 100 of the first embodiment. However, since processing in parameter estimation is different, contents of processing by each unit of a computer 109 is different. In the following, processing in the present embodiment which processing is different from that in the first embodiment will be mainly described.

Note that as an estimation parameter with which a quantitative value can be calculated by utilization of an independent image, there is, for example, a resonance frequency difference $\Delta f_0$. $\Delta f_0$ is used for calculation of an image of magnetic susceptibility.

That is, $\Delta f_0$ is proportional to a phase. Thus, it is possible to acquire a phase image by multiplying each pixel value of a $\Delta f_0$ distribution by a predetermined coefficient. The phase image reflects magnetic susceptibility between tissues. Thus, it is possible to acquire a magnetic susceptibility map by solving an inverse problem based on the phase image.

The $\Delta f_0$ distribution can be calculated when there are two or more images with different TE. Also, a calculation of the $\Delta f_0$ distribution needs a high resolution compared to parameters such as T1, T2, and a.

Thus, in the present embodiment, first, two first reconstructed images with different TE are acquired and a $\Delta f_0$ distribution is calculated from the two images. Then, in a resolution different from that of the first reconstructed images, a scan parameter is changed and a plurality of second reconstructed images is acquired. Subsequently, by a method similar to that of the first embodiment, a different estimation parameter is estimated. Here, the first reconstructed images are converted into a resolution of the second reconstructed images and used. Then, in the present embodiment, the two first reconstructed images with different TE are acquired by a multi echo sequence.

That is, a reconstructed image acquiring unit 220 of the present embodiment acquires first reconstructed images having a first resolution that is an optimal resolution of an estimation parameter with the highest optimal resolution among estimation parameters and second reconstructed images having a second resolution different from the first resolution. It is assumed that the first reconstructed images are multi echo images acquired by the multi echo sequence. Note that the second resolution is the highest resolution among optimal resolutions of the other estimation parameters.

Then, a parameter-estimating unit 230 of the present embodiment estimates, from the multi echo images, a value of $\Delta f_0$ among estimation parameters. Then, the parameter-estimating unit 230 adjusts the resolution of the multi echo images to the second resolution and estimates estimation parameters other than $\Delta f_0$ by using the adjusted multi echo images and the second reconstructed images along with a signal function.

In the following, before a detail description of processing in the parameter-estimating unit 230 of the present embodiment, an imaging sequence of acquiring images with different TE will be described. In the present embodiment, similarly to the first embodiment, an RF-spoiled GE sequence 610 is basically used. In a case of acquiring images with different TE, the multi echo sequence of measuring two or more echo signals in one period of TR is used.

In FIG. 11(a), an RF-spoiled GE sequence of a single echo sequence (hereinafter, referred to as single echo sequence) 610 is illustrated. In FIG. 11(b), an RF-spoiled GE sequence of a multi echo sequence (hereinafter, referred to as multi echo sequence) 630 is illustrated. Note that here, a case of acquiring two echo signals in one period of TR is illustrated as an example of the multi echo sequence 630. Note that in the present drawings, A/D indicates timing of acquiring an echo signal.

The single echo sequence 610 illustrated in FIG. 11(a) is in a manner described with reference to FIG. 4(a). However, in FIG. 11(a), a sequence in a case of three-dimensional imaging is illustrated. Thus, 613 is a magnetic field gradient pulse for slice rephasing and slice phase encoding.

The reconstructed image acquiring unit 220 repeats the above procedure while changing strength of phase encoding magnetic field gradient pulses 613 and 614 (amount of phase encoding ks and kp) and changing an incrementation value of a phase of an RF pulse 612 by 117° (phase of nth RF pulse is θ(n)=θ(n−1)+117n) in repetition time TR and measures echoes necessary for acquiring an image. Each echo is arranged in a three-dimensional k-space (kr-kp-ks space).

Then, the reconstructed image acquiring unit 220 reconstructs an image by the three-dimensional inverse Fourier transform. An image acquired by this pulse sequence 610 is an image in which longitudinal relaxation time (T1) is weighted.

In the multi echo sequence 630 illustrated in FIG. 11(b), an applied pulse is basically similar to that in a case of the single echo sequence 610. That is, first, a radio frequency magnetic field (RF) pulse 612 is emitted along with application of a slice magnetic field gradient pulse 611 and magnetization of a certain slice in an object body is excited. After the slice rephasing and slice phase encoding pulse 613, the phase encoding magnetic field gradient pulse 614, and a readout magnetic field gradient pulse for dephasing 615 are applied, a first magnetic resonance signal (echo signal) 617 is measured during application of a readout magnetic field gradient pulse 616 for addition of positional information in a readout direction.

After the measurement of the echo signal 617, a second echo signal 622 is measured during application of a readout magnetic field gradient pulse 618. Finally, phase encoding magnetic field gradient pulses for dephasing 619 and 620 and a crusher pulse 621 are applied.

In the present sequence 630, time (TE) from the RF pulse 612 is different in the echo signal 617 and the echo signal 622.

The reconstructed image acquiring unit 220 controls an operation similarly to the single echo sequence 610 and respectively arranges the two echo signals 617 and 622 with different TE in different three-dimensional k-spaces. Then, the reconstructed image acquiring unit 220 reconstructs an image from each of the k-spaces by the three-dimensional inverse Fourier transform. Since the two reconstructed images have different TE, degrees of T2 enhancement are different.

[Parameter Estimation Processing]

First, the parameter-estimating unit 230 calculates a $\Delta f_0$ distribution from the two images with different TE.

A rotation (phase) of horizontal magnetization of an excited spin is a value calculated by multiplication of a difference ($\Delta f_0$) between a frequency in a position of the horizontal magnetization and a reference resonance frequency f0 by TE. Thus, when a phase difference between the two images is divided by a difference in TE, $\Delta f_0$ is acquired. This is calculated for each pixel and the $\Delta f_0$ distribution is acquired.

Note that the number of images with different TE is not limited to two. For example, a multi echo sequence in which a readout pulse is further added and three or more echoes with different TE are measured may be used and more images with different TE may be used in calculation of the $\Delta f_0$ distribution. When the number of images is increased, accuracy of calculation of the $\Delta f_0$ distribution is improved. Thus, a sequence of measuring three or more (generally, around five) echo signals in one period of TR is generally used.

The parameter-estimating unit 230 of the present embodiment estimates an estimation parameter including $\Delta f_0$.

As described above, since the parameter-estimating unit 230 performs parameter estimation processing in the first embodiment, images the number of which is equal to or larger than the number of estimation parameters are acquired while values of one or more scan parameters are changed. However, in the present embodiment, the multi echo sequence 630 is executed to calculate the $\Delta f_0$ distribution. By the multi echo sequence 630, it is possible to acquire two or more images with the same scan parameter and different TE. When the number of images acquired by execution of the multi echo sequence 630 for calculation of the $\Delta f_0$ distribution (which image is referred to as multi echo image) is J and the number of estimation parameters is M, images (single image) the number of which is MJ or more are acquired according to the single echo sequence 610 in the present embodiment.

Here, the single image is acquired according to an optimal resolution of an estimation parameter with the highest optimal resolution of a parameter distribution (calculation image) among estimation parameters other than $\Delta f_0$.

Processing thereafter is similar to that in the first embodiment. That is, values of the estimation parameters are serially estimated in order from an estimation parameter with a low optimal resolution and a parameter distribution is acquired. For the estimation, a previously-prepared signal function $f_s$, J multi echo images, and (M-J) single images are used. Here, resolutions of the J multi echo images are adjusted (reduced, here) according to resolutions of the single images.

Note that for example, in the present embodiment, when optimal resolutions of estimation parameters other than $\Delta f_0$ are at the same level or when both of the multi echo images and the single images include adequate SN ratios, the estimation parameter other than $\Delta f_0$ may be estimated without changing of the resolution of the single image.

[Flow of Parameter Estimation Processing]

A flow of the parameter estimation processing of the present embodiment will be described with reference to FIG. 12(a) to FIG. 12(c). Here, there are five estimation parameters that are T1, T2, $B_1$, $\rho S_c$ (=a), and $\Delta f_0$. Then, a case of acquiring a three-dimensional distribution of each estimation parameter by using the single echo sequence 610 and the multi echo sequence 630 will be described as an example. It is assumed that two multi echo images with different TE are acquired in the multi echo sequence 630.

Note that the signal function $f_s$ is previously created by the method described in the first embodiment, or the like.

In this case, similarly to the first embodiment, scan parameter sets 310 in which a value of any of FA, TR, and θ is different and the number of which is larger than the number of estimation parameter to be estimated are also prepared. That is, similarly to the first embodiment, selection is made among twelve imaging parameter sets acquired by combinations of FA being 10° and 30°, θ being 2°, 6°, and 20°, and TR being 10 ms and 40 ms. However, in the present embodiment, two multi echo images are also acquired in the multi echo sequence 630. Thus, five scan parameter sets (P1 to P5) 310 are prepared here although six scan parameter sets (P1 to P6) 310 are prepared in the first embodiment. Accordingly, six images are acquired.

Also, in the multi echo sequence 630, it is not possible to measure an echo with long TE unless TR is moderately long. Thus, the scan parameter sets 310 used in the multi echo sequence 630 are sets with long TR. For example, when the scan parameter sets 310 with TR being 10 ms and 40 ms are prepared, the scan parameter sets 310 with TR being 40 ms are applied to the multi echo sequence 630.

Also, in the example of the first embodiment, TE is fixed to 5 ms. In the present embodiment, in the multi echo sequence 630, TE of a first echo (TE1) is set to 5 ms similarly to the single echo sequence 610 and TE of a second echo (TE2) is set to 20 ms.

Moreover, as described above, $\Delta f_0$ is then used in calculation of a magnetic susceptibility distribution. In the calculation of the magnetic susceptibility distribution, a resolution higher than that of a normal morphological image is necessary. Thus, a scan parameter is set in such a manner that a resolution of images acquired by the multi echo sequence 630 (multi echo image) becomes higher than that of images acquired by the single echo sequence 610 (single echo image).

For example, the scan parameter is preferably set in such a manner that a voxel size indicating a resolution of the multi echo images becomes around 0.5 mm to 1 mm in order to acquire accuracy of calculating a magnetic susceptibility distribution from $\Delta f_0$. Here, the voxel size is 0.8 mm. On the other hand, a resolution of the single echo images is set to 1.6 mm. Here, the resolution is the highest among optimal resolutions of the other estimation parameters T1, T2, $B_1$, and a.

Note that it is assumed that a scan parameter set used in execution of the multi echo sequence 630 is P1 and scan parameter sets used in execution of the single echo sequence 610 are P2 to P5.

Figure 12:
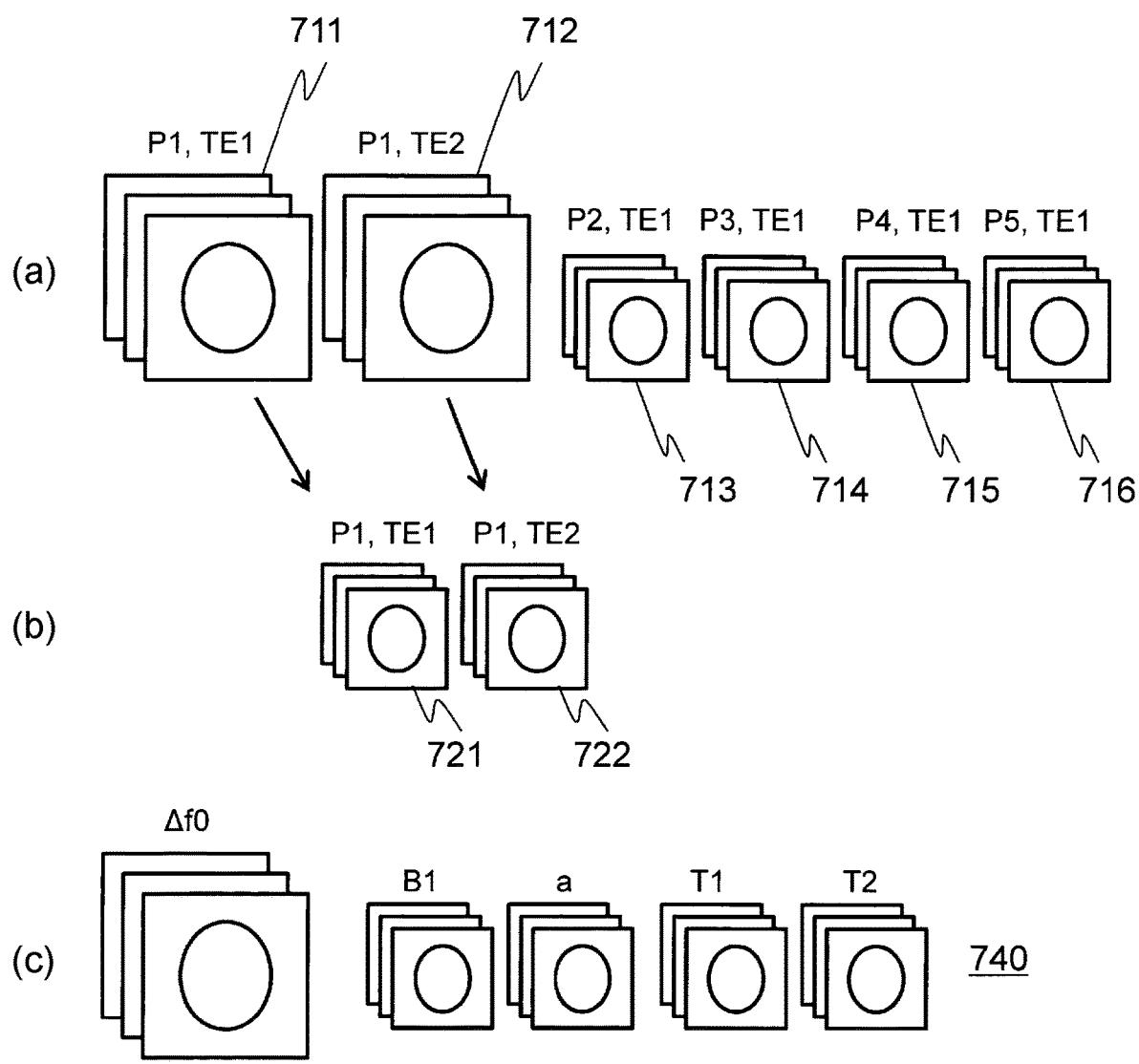
FIG. 12(a) to FIG. 12(c) are views for describing parameter estimation processing of the second embodiment.

Images acquired by utilization of these scan parameter sets are illustrated in FIG. 12(a). In the present drawing, images 711 and 712 are multi echo images acquired by the multi echo sequence 630 and are multi echo images respectively acquired in TE1 and TE2.

Also, images 713 to 716 are single echo images acquired by execution of the single echo sequence 610 with the scan parameter sets P2 to P5. These images 713 to 716 are images acquired in TE1.

The parameter-estimating unit 230 of the present embodiment first estimates $\Delta f_0$ by using the multi echo images 711 and 712.

Then, as illustrated in FIG. 12(b), the parameter-estimating unit 230 converts a resolution of the multi echo images 711 and 712 into a resolution identical to that of the single echo images 713 to 716. Here, the resolution is reduced. It is assumed that multi echo images after the reduction are 721 and 722.

Here, since a voxel size of the multi echo images 711 and 712 is set to be twice of that of the single echo images 713 to 716, for example, 2×2×2 voxels of the multi echo images 711 and 712 are simply added to be 1 voxel. Thus, the reduction of the resolution is realized. Alternatively, linear interpolation or second to third interpolation may be used.

Then, the parameter-estimating unit 230 estimates the estimation parameters $B_1$, a, T1, and T2 by using the previously-prepared signal function $f_s$, the multi echo images 721 and 722, and the single echo images 713 to 716. A method of estimating these estimation parameters is similar to that of the first embodiment. For example, these estimation parameters are estimated by least squares fitting with the above equation (4) and equation (5). Here, similarly to the first embodiment, a $B_1$ map may be first calculated in a low resolution and T1, T2, and a may be calculated in an original resolution.

From the above, as illustrated in FIG. 12(c), a parameter distribution (calculation image) 740 of each of $\Delta f_0$, $B_1$, a, T1, and T2 is acquired.

As described above, the MRI apparatus 100 of the present embodiment includes the parameter-estimating unit 230 similar to that of the first embodiment. Then, the plurality of reconstructed images used in estimation of values of estimation parameters includes the first reconstructed images (711 and 712) having a first resolution that is an optimal resolution of an estimation parameter with the highest optimal resolution among the estimation parameters and the second reconstructed images (713 to 716) having a second resolution different from the first resolution.

Then, the first reconstructed images (711 and 712) are multi echo images acquired by a multi echo sequence. The parameter-estimating unit 230 may estimate, from the multi echo images, a value of a resonance frequency difference $\Delta f_0$ among the estimation parameters. Also, the parameter-estimating unit 230 adjusts the resolution of the multi echo images to the second resolution. Then, by using the adjusted multi echo images and the second reconstructed images (713 to 716) along with the signal function, the parameter-estimating unit 230 estimates values of the estimation parameters other than the resonance frequency difference.

Here, with respect to an estimation parameter with an optimal resolution lower than the second resolution, the parameter-estimating unit 230 may reduce the resolution of the reconstructed images to the optimal resolution of the estimation parameter and estimate the value. Moreover, with respect to the estimation parameters other than $\Delta f_0$, the parameter-estimating unit 230 may serially estimate the value in order from an estimation parameter with a low optimal resolution. In the estimation, a value of an already-estimated estimation parameter may be adjusted to the optimal resolution of the estimation parameter to be estimated and may be used along with the signal function.

In such a manner, similarly to the first embodiment, an intended quantitative value (value of subject parameter and apparatus parameter) can be acquired in an adequate resolution according to the present embodiment. Thus, a calculation image with high quality can be acquired. Also, it is possible to control the number of times of generation of divergence in the estimation and to estimate a value effectively.

Also, in the present embodiment, $\Delta f_0$ is calculated from images in a high resolution which images are acquired by the multi echo sequence. Then, the images in the high resolution is adjusted to a low resolution and is used along with a different low resolution image for estimation of estimation parameters such as T1, T2, $B_1$, and a. In such a manner, it is possible to reduce the number of acquired images for parameter estimation by using the multi echo sequence. Thus, it is possible to improve scanning efficiency compared to a case of performing scanning and estimation separately.

Figure 13:
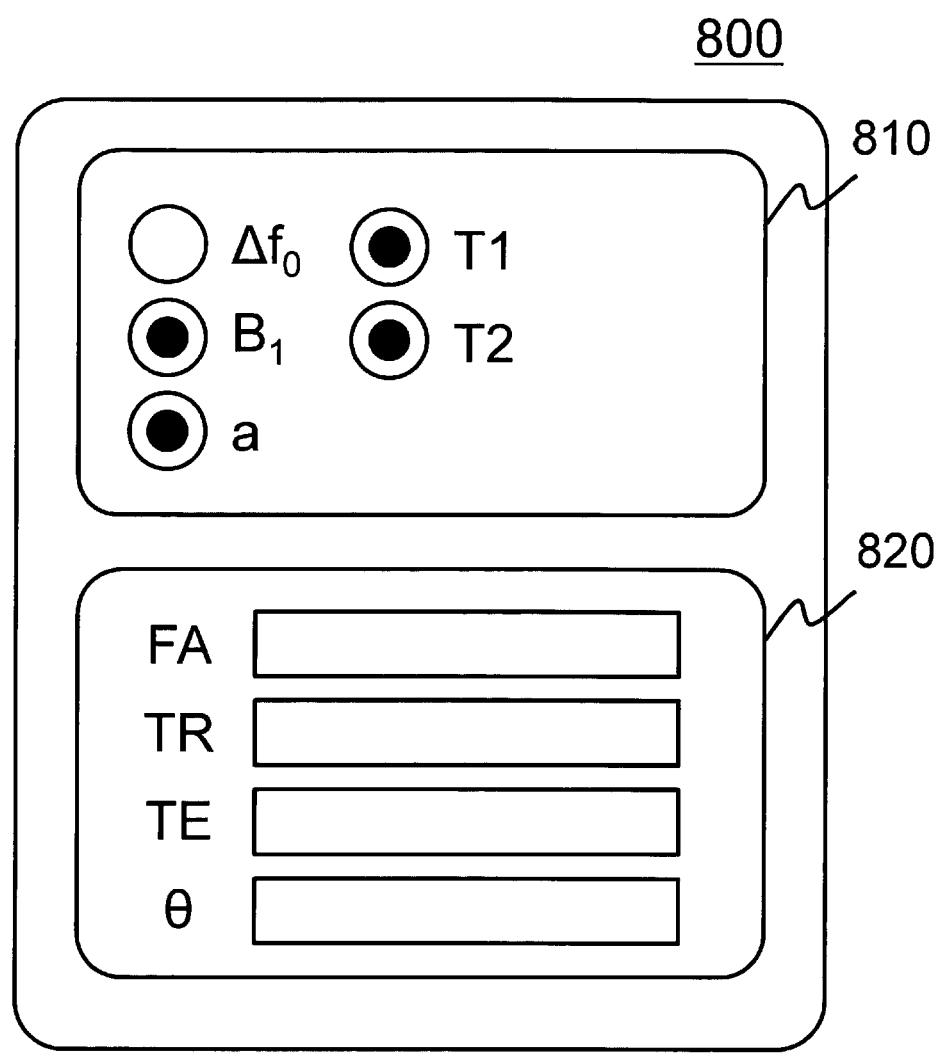
FIG. 13 is a view for describing an example of a receiving screen of each embodiment of the present invention.

Note that in each of the above embodiments, a receiving screen to receive designation of a parameter to be estimated from a user may be included. The receiving screen is generated by the receiving unit 210 and displayed on the display device 110. An example of a receiving screen 800 is illustrated in FIG. 13.

As illustrated in the present drawing, the receiving screen 800 includes, for example, an estimation parameter receiving region 810 to receive designation of an estimation parameter to be estimated, and a parameter set receiving region 820 to receive an imaging parameter set to be set.

The receiving unit 210 receives an instruction from a user and notifies the instruction to the reconstructed image acquiring unit 220 and the parameter-estimating unit 230. According to the received instruction, the reconstructed image acquiring unit 220 acquires an image. The parameter-estimating unit 230 estimates a predetermined estimation parameter according to the instruction.

Here, for example, an estimation parameter, in which an optimal pulse sequence for estimation is previously determined, such as $\Delta f_0$ may be held in a manner associated with the pulse sequence. Accordingly, in a case where a user selects the estimation parameter, even when a pulse sequence is not set, a pulse sequence held in an associated manner is selected automatically.

Modification Example

By using an acquired calculation image and a signal function $f_s$, the display image creating unit 240 of each of the above embodiments can arbitrarily generate images (such as T1-weighted image and T2-weighted image) in which a part of an estimated subject parameter and apparatus parameter, a pulse sequence, and a scan parameter is changed.

However, a changeable pulse sequence is an arbitrary pulse sequence in which a signal function $f_s$ is already known or already created by numerical simulation.

In the following, a case of using a spin-echo (SE) sequence that is the most general as a pulse sequence will be described as an example. First, the SE sequence will be described. FIG. 14(*a*) is a view illustrating an example of an SE sequence 900.

In the SE sequence 900, first, a radio frequency magnetic field (RF) pulse 902 is emitted along with application of a slice selecting magnetic field gradient pulse 901 and magnetization of a certain slice in an object body is excited. Then, a slice rephasing magnetic field gradient pulse 903, a phase encoding magnetic field gradient pulse 904 for addition of positional information in a phase encoding direction to a phase of magnetization, and a readout magnetic field gradient pulse for dephasing 905 are applied. Then, after application of crusher pulses 906, 907, and 908 for controlling an unnecessary signal to each axis, a refocusing pulse 910 is emitted along with a slice selecting magnetic field gradient pulse 909 and crusher pulses 911, 912, and 913 are applied. Then, while a readout magnetic field gradient pulse 914 for addition of positional information in a readout direction is applied, an echo signal 918 is measured by A/D 915. Finally, crusher pulses 916 and 917 are applied. A period from emission of the RF pulse 902 to an echo peak is called echo time TE.

The above procedure is repeatedly performed in repetition time TR with strength of the phase encoding magnetic field gradient pulse 904 (amount of phase encoding kp) and a slice position being changed and an echo signal for the number of necessary slices is measured. The slice position is changed by a frequency of the RF pulse 902.

As illustrated in FIG. 14(*b*), each echo signal 918 is arranged in a k-space slice with respect to each slice and an image is reconstructed by the inverse Fourier transform.

In this SE sequence 900, TR and TE are arbitrarily changed, whereby an image with a contrast in which T1 is weighted (T1-weighted image) or an image with a contrast in which T2 is weighted (T2-weighted image) is acquired. For example, when TR is set to a several hundred milliseconds and TE is set to about ten milliseconds, a T1-weighted image is acquired. Also, when TR is set to a several seconds and TE is set to about a hundred milliseconds, a T2-weighted image is acquired.

A signal function of the SE sequence 900 is analytically calculated and an intensity value $IS_E$ of an image scanned by the SE sequence 900 is expressed by the following equation (6).

[Math 6]

$$I_{SE}=a(1-\exp(-TR/T1))\exp(-TE/T2)\times\sin(B_1\times 90°) \quad (6)$$

In the equation (6), it is possible to freely create the T1-weighted image and the T2-weighted image in an arbitrary degree of enhancement by using the estimated subject parameters T1 and T2 and designating values of TR and TE of the scan parameters. Also, by setting $B_1$, which is one of subject parameters, uniformly (for example, setting $B_1=1$), it is possible to acquire an image of when a $B_1$ distribution is uniform.

Also, for example, when the subject parameters T1 and T2 estimated in each of the above embodiments are used and in a case where TR is 500 ms and TE is set to 15 ms, the T1-weighted image is acquired. In the T1-weighted image acquired by the SE sequence 900, an intensity value becomes small when T1 becomes long. For example, when TE is kept as 15 ms and TR is reduced to 100 ms, a contrast is enhanced and a T1-weighted image in which a degree of T1 enhancement is increased is acquired.

On the other hand, when TR and TE are made longer (for example, (TR, TE)=(4000 ms, 100 ms)), the T2-weighted image is acquired. In the T2-weighted image, an intensity value becomes large when T2 becomes long.

Note that a pulse sequence is not limited to the SE sequence 900. The object only needs to be a sequence, in which a signal function $f_s$ is analytically acquired or can be created by numerical simulation as described above, such as a gradient echo sequence or an RSSG sequence.

Note that when the signal function $f_s$ is not known or not created by the numerical simulation, an image may be created by numerical simulation with a set pulse sequence, scan parameter, subject parameter, and apparatus parameter.

In such a manner, according to the present modification example, by using a value of an estimated estimation parameter and a signal function of a predetermined pulse sequence, it is possible to acquire an image having predetermined image quality (arbitrary contrast) of the pulse sequence.

Note that in each of the above embodiments, the parameter-estimating unit 230, the display image creating unit 240, and the signal function creating unit 250 are included in the MRI apparatus 100. However, this is not the limitation. At least one of these configurations may be constructed, for example, on an information processing apparatus that can transmit/receive data to/from the MRI apparatus 100 and that is independent from the MRI apparatus 100.

REFERENCE SIGNS LIST

100 MRI apparatus
101 magnet
102 gradient coil
103 subject
104 sequencer
105 magnetic field gradient power supply
106 radio frequency magnetic field generator
107 transmitter/receiver coil
108 receiver
109 computer
110 display device 111 storage device
210 receiving unit
220 reconstructed image acquiring unit
230 parameter-estimating unit
240 display image creating unit
250 signal function creating unit
310 scan parameter set
320 reconstructed image
321 image adjusted to low resolution
330 signal function
340 parameter distribution
341 parameter distribution
342 parameter distribution after interpolation enlargement
343 parameter distribution
344 parameter distribution by conventional method
410 scan parameter set
420 signal function
513 profile of $B_1$ distribution
514 profile of $B_1$ distribution
523 profile of a distribution
524 profile of a distribution
610 RF-spoiled GE sequence
611 slice magnetic field gradient pulse
612 RF pulse
613 magnetic field gradient pulse for slice rephasing (and slice phase encoding)
614 phase encoding magnetic field gradient pulse
615 readout magnetic field gradient pulse for dephasing
616 readout magnetic field gradient pulse
617 echo signal
618 readout magnetic field gradient pulse
619 phase encoding magnetic field gradient pulse for dephasing
620 phase encoding magnetic field gradient pulse for dephasing
621 crusher pulse
622 echo signal
630 multi echo sequence
711 multi echo image
712 multi echo image
713 single echo image
714 single echo image
715 single echo image
716 single echo image
721 multi echo image
722 multi echo image
740 parameter distribution
800 receiving screen
810 estimation parameter receiving region
820 parameter set receiving region
900 SE sequence
901 slice selecting magnetic field gradient pulse
902 RF pulse
903 slice rephasing magnetic field gradient pulse
904 phase encoding magnetic field gradient pulse
905 readout magnetic field gradient pulse for dephasing
906 crusher pulse
907 crusher pulse
908 crusher pulse
909 slice selecting magnetic field gradient pulse
910 refocusing pulse
911 crusher pulse
912 crusher pulse
913 crusher pulse
914 readout magnetic field gradient pulse
915 A/D
916 crusher pulse
918 echo signal

The invention claimed is:

1. A magnetic resonance imaging apparatus comprising:
a processor; and
a memory storing thereon a program, which when executed by the processor performs the step of:
estimating a value of at least two estimation parameters among two or more subject parameters depending on a subject and one or more apparatus parameters depending on an apparatus by using a plurality of reconstructed images and a signal function of a pulse sequence followed in acquiring the reconstructed images, the at least two estimation parameters including at least two of longitudinal relaxation time (T1), transverse relaxation time (T2), spin density ($\rho$) and radio frequency magnetic field strength $B_1$,
wherein the plurality of reconstructed images is acquired by imaging performed according to the pulse sequence with a plurality of scan parameter sets,
wherein the signal function is a function defining, for each of the pulse sequences, a relationship between each pixel value of the reconstructed images and the scan parameters, the subject parameters, and the apparatus parameters in each pulse sequence, and
wherein the estimation of the value of the at least two estimation parameters is performed by using a reconstructed image in a predetermined resolution with respect to each of the at least two estimation parameters based on a signal-to-noise ratio of the reconstructed image corresponding to each parameter, respectively,
wherein the plurality of reconstructed images has a resolution that is the highest resolution among predetermined resolutions of the at least two estimation parameters, and
wherein the program, when executed by the processor further performs the steps of:
reducing, with respect to a first estimation parameter having a first predetermined resolution lower than the highest resolution, a resolution of the reconstructed images by interpolation enlargement to the first predetermined resolution of the first estimation parameter and estimates the value;
estimating the value for a second estimation parameter after estimating the value of the first estimation parameter with the first predetermined resolution;
adjusting a value of an already-estimated second estimation parameter to a second predetermined resolution of the second estimation parameter to be estimated and uses the adjusted value along with the signal function during the estimation;
repeating the steps of estimating and adjusting for any remaining estimation parameters, wherein estimation parameters that have the same predetermined resolution are estimated simultaneously; and
acquiring, by using the estimated values of the at least two estimation parameters and a signal function of a predetermined pulse sequence, an image with predetermined image quality of the pulse sequence,
wherein the number of reconstructed images is equal to or larger than the number of the at least two estimation parameters, and
wherein the signal function is generated by execution of a numerical simulation with respect to each combination of the plurality of different scan parameters and subject parameters and by interpolation of an acquired result.

2. The magnetic resonance imaging apparatus according to claim 1, wherein the first estimation parameter is radio frequency magnetic field strength ($B_1$), and the second estimation parameter is longitudinal relaxation time (T1).

3. The magnetic resonance imaging apparatus imaging apparatus according to claim 1, wherein the at least two estimation parameters include at least two of longitudinal relaxation time (T1), transverse relaxation time (T2), and spin density ($\rho$).

4. The magnetic resonance imaging apparatus according to claim 1, wherein the plurality of reconstructed images includes a first reconstructed image having a first resolution that has a predetermined resolution of an estimation parameter with the highest resolution among the estimation parameters, and a second reconstructed image having a second resolution different from the first resolution.

5. The magnetic resonance imaging apparatus according to claim 4, wherein the first reconstructed image is a multi echo image acquired by a multi echo sequence, and the estimating of the value includes estimating, from the multi echo image, a value of a resonance frequency difference among the estimation parameters.

6. The magnetic resonance imaging apparatus according to claim 1, wherein in the plurality of scan parameter sets, a value of at least one of repetition time, strength of a radio frequency magnetic field, and a phase of the radio frequency magnetic field among the imaging parameters is different from each other.

7. The magnetic resonance imaging apparatus according to claim 1, wherein the program, when executed by the processor further performs the step of: receiving an instruction of the estimation parameters, receiving setting of the at least two estimation parameters through an estimation parameter receiving screen, and wherein the acquiring of the reconstructed image according to a scanning condition including a predetermined resolution is dependent upon the received at least two estimation parameters previously held.

\* \* \* \* \*